United States Patent
Slack-Davis et al.

(10) Patent No.: US 9,606,123 B2
(45) Date of Patent: Mar. 28, 2017

(54) COMPOSITIONS AND METHODS FOR DIAGNOSING AND MONITORING OVARIAN CANCER PROGRESSION AND TREATMENT

(71) Applicants: Jill K. Slack-Davis, Free Union, VA (US); Kimberly A. Kelly, Crozet, VA (US)

(72) Inventors: Jill K. Slack-Davis, Free Union, VA (US); Kimberly A. Kelly, Crozet, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 147 days.

(21) Appl. No.: 14/228,828

(22) Filed: Mar. 28, 2014

(65) Prior Publication Data

US 2014/0294730 A1 Oct. 2, 2014

Related U.S. Application Data

(60) Provisional application No. 61/806,437, filed on Mar. 29, 2013.

(51) Int. Cl.
| | | |
|---|---|---|
| *A61K 51/00* | (2006.01) | |
| *A61M 36/14* | (2006.01) | |
| *G01N 33/574* | (2006.01) | |
| *A61K 51/08* | (2006.01) | |

(52) U.S. Cl.
CPC ..... *G01N 33/57449* (2013.01); *A61K 51/088* (2013.01); *G01N 2333/70542* (2013.01); *G01N 2800/52* (2013.01)

(58) Field of Classification Search
CPC ........ A61K 38/00; A61K 51/00; A61K 51/08; A61K 51/088; G01N 33/57449; G01N 2333/70542; G01N 2800/52
USPC .... 424/1.11, 1.65, 1.69, 9.1, 9.2; 514/1, 1.1, 514/19.2, 19.3, 21.6; 530/300, 328
See application file for complete search history.

(56) References Cited

U.S. PATENT DOCUMENTS 7,666,979 B2    2/2010   Fan et al.

FOREIGN PATENT DOCUMENTS

| WO | 2009/129220 | 10/2009 |
|---|---|---|
| WO | 2011/057078 | 5/2011 |

OTHER PUBLICATIONS

Fung-Kee-Fung et al (Current Oncology, 2007, vol. 14, No. 5, pp. 195-208).*
Slack-Davis et al (Cancer Research, 2009, vol. 69, No. 4, pp. 1469-1476).*
Li, Z., et al., "64 Cu-Labeled Tetrameric and Octameric Rgd Peptides for Small Animal PET of Tumor αvβ3 Integrin Expression", Journal of Nuclear Med., 2007:48: 1162-1171.
Janssen, J., et al., "Comparison of a Monomeric and Dimeric Radiolabeled RGD-Peptide for Tumor Targeting", Cancer Biotherapy & RadioPharma, V17, No. 6, 2002, 641-646.
Poethko, T., et al., "Two-Step Methodology for High-Yield Routine Radiohalogenation of Peptides: 18 F-Labeled RGD and Octreotide Analogs", Jrnl. of Nuclear Med., 2004: 45: 892-902.
Chen, X., et al., "MicroPET and Autoradiographic Imaging of Breast Cancer αv-Integrin Expression Using 18F- and 64 Cu-Labeled RGD Peptide", Bioconjugate Chem., 2004, 15: 41-49.
Chen, X., et al., "Pharmacokinetics and tumor retention of 125 I-labeled RGD peptide are improved by PEGylation", Nuclear Med. & Biology, 31 2004, 11-19.
Nahrendorf, M., et al., "18 F-4V for PET-CT Imaging of VCAM-1 Expression in Atherosclerosis", JACC: Cariovasc. Imag., 2:10: 1213-1222.
Scalici, J., et al., "Imaging VCAM-1 as an Indicator of Treatment Efficacy in Metastatic Ovarian Cancer", J. Nucl. Med., Nov. 2013, 54: 1883-1889.
Kelly, K., et al., "In Vivo Phage Display Selection Yields Atherosclerotic Plaque Targeted Peptides for Imaging", Molecular Imag. Biology, 2006, 8: 201-207.
Kelly, K., et al., "In Vivo Imaging of Molecularly Targeted Phage", Neoplasia, 2006, 1011-1018.

* cited by examiner

*Primary Examiner* — D L Jones
(74) *Attorney, Agent, or Firm* — Rodney L. Sparks

(57) ABSTRACT

The present invention provides compositions and methods useful for diagnosing, monitoring the progression, identifying the location, and monitoring the treatment response in ovarian cancer based on detecting and locating VCAM-1 expression.

13 Claims, 12 Drawing Sheets

| Patient Characteristics | Stage I/II | Stage III/IV | p-value |
|---|---|---|---|
| Number | 26 | 30 | ------- |
| Age (median) | 56 | 60 | ns |
| Histology (%) | | | |
| Serous | 10 (38) | 25 (83) | <0.001 |
| Endometrioid | 7 (27) | 1 (3) | |
| Mucinous | 2 (8) | 1 (3) | |
| Clear Cell | 4 (15) | 2 (7) | |
| Mixed | 3 (12) | - | |
| Carcinosarcoma | --- | 1 (3) | |
| Other | --- | -- | |
| Treatment Approach (%) | | | |
| Primary Surgery | 25 (96) | 26 (87) | ------- |
| NACT | 1 (4) | 4 (13) | |
| Surgical Cytoreduction (%) | | | |
| Optimal | 26 (100) | 18 (60) | ------- |
| Suboptimal | 0 (0) | 9 (30) | |

COMPOSITIONS AND METHODS FOR DIAGNOSING AND MONITORING OVARIAN CANCER PROGRESSION AND TREATMENT

CROSS REFERENCE TO RELATED APPLICATIONS

This application is entitled to priority pursuant to 35 U.S.C. §119(e) to U.S. provisional patent application No. 61/806,437, filed on September March 29, 2013. The entire disclosure of the afore-mentioned patent application is incorporated herein by reference.

STATEMENT REGARDING FEDERALLY SPONSORED RESEARCH OR DEVELOPMENT

This invention was made with government support under Grant Nos. R01 CA 142783, awarded by The National Institutes of Health. The government has certain rights in the invention.

BACKGROUND

The current standard of care in the US for women with advanced ovarian cancer is upfront surgical cytoreduction followed by systemic chemotherapy. There is extensive retrospective data to support aggressive surgery as important in improving overall survival. Some women, however, will present with disease that is not resectable (for example, intra-parenchymal liver metastases) or will be too medically ill to undergo surgery safely, without significant morbidity. In these cases, neoadjuvant chemotherapy has been shown to allow optimal cytoreduction without significant morbidity. However, not all women in either scenario (i.e., upfront surgery or neoadjuvant chemotherapy) will achieve first remission, and some will suffer disease progression during primary therapy. For women with platinum-resistant or refractory disease, extensive surgical efforts will not likely impact survival. Currently, it is not possible to identify these patients pre-operatively.

Presently, CA125, the only marker for ovarian cancer, is approved for use to assess treatment response. However, levels of CA125 are not predictive of successful cytoreduction. Moreover, some patients will experience recurrence without a rise in CA125, and recent data suggests that rising CA125 in the setting of recurrent disease is not useful in identifying the appropriate time to start treatment. Finally, it has been noted that the traditional disease response to treatment as measured by CT scan and CA125 may not apply to the newer biologic therapies. There is, therefore, a need to identify new markers to guide treatment decisions at different phases of this disease.

Vascular cell adhesion molecule-1 (VCAM-1) has been identified as a regulator of ovarian cancer peritoneal metastasis (Slack-Davis et al., 2009, Cancer Res.). Importantly, VCAM-1 is known to be expressed preferentially on the mesothelium of ovarian cancer patients compared to women with benign disease. Moreover, inhibition of VCAM-1 function decreases mesothelial invasion, diminishes tumor burden and increases survival in a mouse model of metastatic ovarian cancer.

Ovarian cancer is frequently diagnosed in advanced stage with extensive peritoneal metastasis and a 5-year survival of <25%. Platinum-resistance is a significant obstacle to successful treatment of ovarian cancer, and the inability to accurately monitor treatment response further confounds management of women with this disease.

There is a long felt need in the art for compositions and methods useful for diagnosing ovarian cancer, establishing treatment regimens for platinum-sensitive or platinum-resistant ovarian cancer, monitoring the progression of ovarian cancer, and monitoring the treatment response in ovarian cancer. The present application satisfies these needs.

SUMMARY OF THE INVENTION

It is disclosed herein that vascular cell adhesion molecule-1 (VCAM-1), an adhesion receptor expressed in the metastatic ovarian cancer microenvironment, is expressed at the earliest stages of peritoneal metastasis and mirrors tumor response to platinum-based chemotherapy, that is, it decreases when platinum-sensitive tumors are treated but does not change when platinum-resistant tumors are present in the subject. Immunohistochemical (IHC) staining of peritoneal or omental biopsies from women undergoing surgery for ovarian cancer revealed an increased likelihood of VCAM-1 expression among women with tumor implantation at secondary sites, whether restricted to the pelvis (Stage II) or throughout the peritoneal cavity (Stage III). That is, it was not found in Stage I cancer but was found in Stage II on. Additionally, VCAM-1 expression was inversely associated with patient exposure to chemotherapy. The present invention therefore encompasses the use of VCAM-1 as a marker of treatment response and for developing treatment regimens.

It is disclosed herein using a mouse model of peritoneal ovarian cancer metastasis and VCAM-1-specific single photon emission computed tomography (SPECT) imaging probes, concomitant decreases in VCAM-1 expression and tumor burden occur following carboplatin treatment of mice bearing platinum-sensitive cells; neither was altered in mice with platinum-resistant tumors. Together these observations indicate that 1) VCAM-1 is expressed early in the course of ovarian cancer metastatic progression; 2) it reflects treatment response; and 3) its expression is correlated with tumor stage.

Based on the disclosure provided herein, the present invention encompasses, inter alia, using VCAM-1 imaging probes to monitor treatment response in ovarian cancer patients, thus providing the potential to improve management of women with this disease. The present invention provides a method of early detection of women not responding to treatment and provides an opportunity to offer alternative therapies and to avoid unnecessary side effects. Furthermore, the present invention provides compositions and methods for detecting and measuring VCAM-1 and using it as a marker of metastasis, cancer progression, and effectiveness of treatment of ovarian cancer where VCAM-1 expression is associated with the cancer or its metastasis. In one aspect, VCAM-1 is expressed by mesothelial cells. In one aspect, the cancer is ovarian cancer. In one aspect, the method is useful for developing a treatment regimen or selecting a therapy for a subject based on the results of detecting and measuring VCAM-1 in the subject. It will be appreciated by one of skill in the art that in addition to the methods disclosed herein for detecting and measuring VCAM-1, other methods can be used as well. For example, expression can be measured based on mRNA or protein levels and can be done using in vivo non-invasive techniques or ex vivo techniques with a sample obtained from a subject.

In one embodiment, the present invention encompasses detecting and monitoring VCAM-1 as a molecular indication of chemosensitivity to platinum-based chemotherapy.

The present invention therefore allows for earlier detection of platinum resistant disease compared to current methods and allows for alterations in treatment regimen directed at the molecular behavior of disease.

In one embodiment, the present invention provides compositions and methods for differentiating platinum-sensitive metastatic ovarian cancer from platinum-resistant metastatic ovarian cancer. In one aspect, the method comprises administering an effective amount of a platinum-based chemotherapeutic agent to a subject with ovarian cancer, determining the level of VCAM-1 expression in the subject following administration and then comparing the VCAM-1 level to the level of VCAM-1 expression in the subject prior to administration of the chemotherapeutic agent or comparing it to a standard value of VCAM-1 levels. A decrease in VCAM-1 levels following administration of the platinum-based chemotherapeutic agent is an indication that the ovarian cancer is platinum-sensitive and no change in VCAM-1 levels is an indication that the ovarian cancer is platinum-resistant. In one aspect, once it has been distinguished what type of cancer it is, a diagnosis of platinum-sensitive or platinum-resistant is made. In one aspect, once a diagnosis is made the subject or physician is notified and a treatment regimen is designed and implemented based on whether the subject has a platinum-sensitive or platinum-resistant metastatic ovarian cancer. In one aspect, the VCAM-1 levels in the subject are determined by administering to the subject an effective amount of a VCAM-1 imaging probe that binds to VCAM-1 or contacting a biopsy from the subject with an effective amount of a VCAM-1 imaging probe, and then determining the amount of VCAM-1 levels in the subject or in the biopsy.

In one embodiment, one the type of ovarian cancer has been determined and it has been distinguished whether it is platinum-sensitive or platinum-resistant, a diagnosis is made. In one aspect, the subject or a treating physician is notified of the diagnosis. In one aspect, the treating physician will begin treatment or establish a treatment regimen based on the diagnosis.

In one embodiment, the present invention provides compositions and methods for treating a subject with platinum-sensitive or platinum-resistant ovarian cancer. In one embodiment, the method comprises administering an effective amount of at least one dose of a platinum-based chemotherapeutic agent to a subject with ovarian cancer to determine whether the cancer is platinum-sensitive. In one aspect, sensitivity is determined by measuring the level of VCAM-1 expression or levels in the subject following administration of at least of dose of a platinum-based chemotherapeutic agent, determining the VCAM-1 levels after administration and then comparing the post-administration VCAM-1 levels to a level of VCAM-1 expression in the subject that was determined prior to administration of the chemotherapeutic agent or comparing to a standard value of VCAM-1 levels. A decrease in VCAM-1 levels following administration of the platinum-based chemotherapeutic agent is an indication that the ovarian cancer is platinum-sensitive and that platinum-based therapy should be continued. No change in VCAM-1 levels is an indication that the ovarian cancer is platinum-resistant and that a non-platinum-based therapy should be developed for the subject.

In one embodiment, the invention provides a method for establishing a treatment regimen for a subject with metastatic ovarian cancer once it has determined whether the tumor is platinum-sensitive or platinum-resistant and a diagnosis has been made and communicated to a treating physician. In one aspect, the method comprises administering a pharmaceutical composition comprising an effective amount of at least one dose of a platinum-based chemotherapeutic agent to a subject with ovarian cancer, determining the level of VCAM-1 expression in the subject following administration and comparing the resulting VCAM-1 level to the level of VCAM-1 expression in the subject prior to administration of the chemotherapeutic agent or to a standard value of VCAM-1 levels. A decrease in VCAM-1 levels following administration is an indication that the ovarian cancer is platinum-sensitive and that platinum-based therapy should be continued and no change in VCAM-1 levels is an indication that the ovarian cancer is platinum-resistant and that a non-platinum-based therapy should be used on the subject. In one aspect, the pharmaceutical composition administered to the subject optionally comprises at least one chemotherapeutic agent that is non-platinum-based and optionally comprises an additional therapeutic agent.

Platinum-based chemotherapeutic agents useful in the practice of the invention, include, but are not limited to, cisplatin, carboplatin, oxaliplatin, satraplatin, picoplatin, nedaplatin, triplatin, and lipoplatin. In one embodiment, carboplatin is administered intravenously for a time period of at least about 5 minutes. One of ordinary skill in the art will appreciate that the dosage of carboplatin or other platinum-based chemotherapeutic agent is based on health, weight, body size, and response to therapy and that these can be used in conjunction with a known dose calculator. For example, some recent guidelines suggest that the maximum dose is based on a glomerular filtration rate (GFR) estimate that is capped at 125 mL/min for patients with normal renal function and that no higher estimated GFR values should be used.

In general, courses of carboplatin treatment are not given more often than once every four weeks, but can be varied. It can be administered, for example, about once a week, once every two weeks, once every three weeks, once every four weeks, once every five weeks, once every six weeks, once every eight weeks and once every ten weeks. The aforementioned timing regimen is not meant to be exhaustive or exclusive and can include administering the agent at least twice per each time frame, etc.

In one embodiment, the progression of ovarian cancer or monitoring the treatment of cancer is performed by administering VCAM-1 targeting compositions of the invention at various times and detecting, locating, and measuring VCAM-1 at those time points. In one aspect, platinum-based chemotherapeutics are used. In one aspect, the chemotherapeutic agent is carboplatin. One of ordinary skill in the art will appreciate that other platinum-based chemotherapeutics that elicit the same response as carboplatin can be used in the methods of the invention.

In one embodiment, the present invention provides compositions and methods for predicting responsiveness to platinum-based chemotherapy in a test subject with ovarian cancer. In one aspect, the method comprises administering an effective amount of a platinum-based chemotherapeutic agent to the test subject, determining the level of VCAM-1 expression in the subject after the agent is administered and comparing the level after administration to the level of VCAM-1 expression in the subject prior to administration of the agent or to a standard value of VCAM-1 levels. A decrease in VCAM-1 levels following administration of the platinum-based chemotherapeutic agent is an indication that the ovarian cancer is platinum-sensitive and no change in VCAM-1 levels is an indication that the ovarian cancer is platinum-resistant. Therapy can be designed based on these results.

In one embodiment, the level and location of detected VCAM-1 is quantified with an analytical device and program. In one aspect, the level and location of detected VCAM-1 is compared with the level and location in a control sample. In one embodiment, detection comprises the steps described herein and further comprises analyzing the results with an analytical device and program. In one aspect, the analytical device comprises a computer.

The present invention further provides compositions and methods useful for personalized medicine. In one embodiment, the present invention provides compositions and methods useful for selecting a subject with cancer who will be responsive to treatment.

In one embodiment, the present invention provides for the detection of VCAM-1 using a multimeric peptide ligand complex for binding to VCAM-1 or a homolog or fragment thereof. In one aspect, each of the peptides of the multimer is independently and optionally coupled to polyethylene glycol. In one aspect, each of the peptides of the multimer or peptides optionally coupled to polyethylene glycol is further coupled to a chelating agent. Optionally the chelating agent is coupled by at least one linker to the peptides or peptides optionally coupled to polyethylene glycol. Optionally, at least one imaging agent is coupled to the chelating agent and optionally at least one therapeutic agent is coupled to the chelating agent.

In one embodiment, the multimeric complex directed against VCAM-1 is a tetramer, has the formula [(VHPKQHRGGSPEG5K)4K]2-KK(DOTA)-βA-NH$_2$, and is referred to as a tetrameric VCAM-1 targeted peptide (tVCAM-4). One of skill in the art will appreciate that the present invention is not limited to the use of the multimeric complexes as described herein and that the complexes can be modified as long as the complexes can still effectively target VCAM-1 and be imaged or localized well enough to satisfy the needs of detecting, localizing, or measuring VCAM-1 as described herein. One of ordinary skill in the art will appreciate that some modification of the multimer can also be useful.

The peptide of probe tVCAM-4 as used herein has the sequence VHPKQHRGGS (SEQ ID NO:1).

The invention further provides a method for detecting VCAM-1 or a homolog or fragment thereof in a subject. The method comprises administering to a subject a multimeric peptide ligand complex comprising an imaging agent, and detecting the location of cells comprising VCAM-1 using a suitable method for detecting and measuring VCAM-1.

In one embodiment, mesothelial VCAM-1 expression correlates with tumor stage. In one aspect, detection of VCAM-1 expression indicates that the ovarian cancer is at least stage II. In one embodiment, the cancer is a metastatic cancer.

The invention is also useful for determining the stage of carcinogenesis of a cancer and monitoring its progression from early to late stage cancer. This method is useful for determining the type and amount of therapy to use.

Peptides of the invention, such as those having a sequence of SEQ ID NO:1, are useful in forming the peptide ligand multimers of the invention. Additionally, the multimers can be modified by the addition of amino acids such as beta alanine (βA) and polyethylene glycol to increase stability, half-life in the blood stream and tissues, decrease degradation, etc. One of ordinary skill in the art will appreciate that the orientation of the sequences in the complex can in some cases be changed and that the multimer can be a heteromultimer or a homomultimer.

In one aspect, the multimeric peptide ligand complex is a homomultimer or a heteromultimer. In one aspect, the homomultimer is a tetramer.

In one embodiment, the multimeric peptide ligand complex comprises a chelator selected from the group consisting of DTPA, DO3A, DOTA, EDTA, TETA, EHPG, HBED, NOTA, DOTMA, DFO, TETMA, PDTA, TTHA, LICAM, HYNIC, and MECAM.

In one aspect, the polyethylene glycol is polyethylene glycol 5000.

In one aspect, the method provides for the use of an imaging agent selected from the group consisting of a radionuclide, a radiological contrast agent, a paramagnetic ion, a metal, a biological tag, a fluorescent label, a chemiluminescent label, an ultrasound contrast agent and a photoactive agent. One of ordinary skill in the art will understand that the method of detection used will depend on the particular imaging agent used.

In one embodiment, the multimeric peptide ligand complex comprises an imaging agent selected from the group consisting of a radionuclide, a radiological contrast agent, a paramagnetic ion, a metal, a biological tag, a fluorescent label, a chemiluminescent label, an ultrasound contrast agent and a photoactive agent. In one aspect, the imaging agent is a radionuclide. In one aspect, the radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, and other gamma-, beta-, or positron-emitters. In one aspect, the radionuclide is $^{111}$In. In one aspect, the imaging agent is detected with a SPECT/CT scanner coupled to a computer, and analyzing imaging data using a program to quantify or compare levels of VCAM-1.

The invention further provides kits for diagnosing, detecting, imaging, and treating ovarian cancers.

Various aspects and embodiments of the invention are described in further detail below.

DETAILED DESCRIPTION

Abbreviations and Acronyms

Figures 1A, 1B:
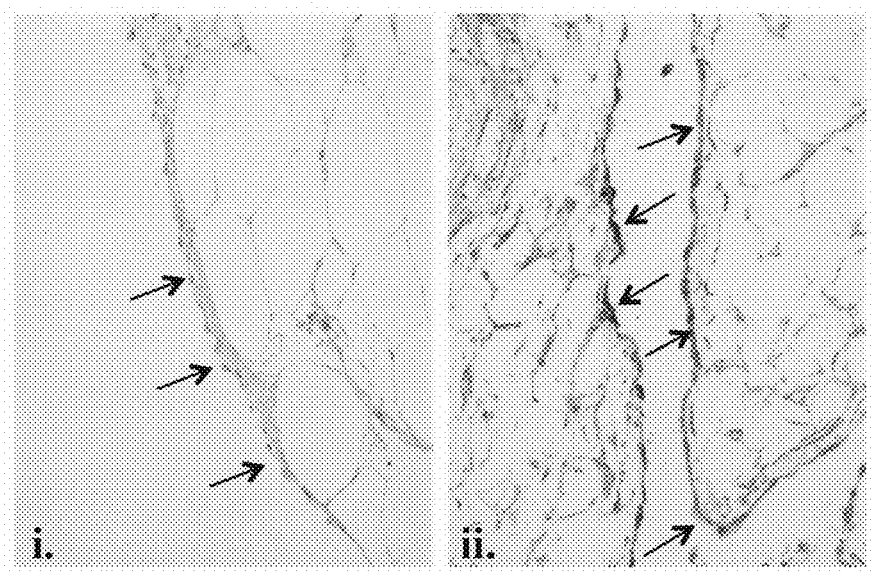
FIG. 1. Peritoneal VCAM-1 expression among women with ovarian cancer. (A) Characteristics of patients selected for the retrospective analysis. The number of patients (percentage of the total in parentheses) with the indicated tumor histology, treatment approach and the ability to achieve optimal surgical cytoreduction are shown as well as the median age of each group. NACT—neoadjuvant chemotherapy. (B) Representative histology of biopsies stained for VCAM-1 expression. Arrows indicate mesothelium. i—example of negative staining; ii—brown staining of mesothelium indicates positive reactivity. (C) Incidence of women with positive VCAM-1 staining of the mesothelium segregated by tumor stage. Omentum or peritoneal biopsies were stained for VCAM-1 using IHC. Specimens were scored positive if >50% of the mesothelial cells showed reactivity (stippled bars) or negative if <50% of the cells showed reactivity (solid grey). Data represent percent of total patients analyzed. Stage I, n=12, Stage II, n=14, Stage III/IV, n=22. (D) Percentage of specimens with VCAM-1 positivity among Stage II patients separated based on presence (peritoneal involvement, n=7) or absence (local growth, n=7) of secondary tumor implants within the pelvis. (E) Percentage of VCAM-1 staining specimens from a set of matched Stage III patients who received upfront surgery (no treatment, n=18) or neoadjuvant chemotherapy (NACT, n=13).

A2780—platinum-sensitive cell line
A2780Cis—platinum-resistant cell line
βA—beta alanine
CNR—contrast to noise ratio
CT—computed tomography
DFO—desferoxamine (chelator)
DOTA—1,4,7,10-tetraazacyclododecane-1,4,7,10-tetraacetic acid
GFR—glomerular filtration rate
LP9—mesothelial cell line
MRI—magnetic resonance imaging
NER—normalized enhancement ratio.
NIR—near infrared
NIRF—near infrared fluorochrome
PET—positron emission tomography
SPECT—single photon emission computed tomography
SKOV3ip1—platinum-resistant cell
tVCAM-4—tetrameric VCAM-1 targeted peptide
VCAM-1—vascular cell adhesion molecule-1

DEFINITIONS

In describing and claiming the invention, the following terminology will be used in accordance with the definitions set forth below.

The articles "a" and "an" are used herein to refer to one or to more than one (i.e. to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

As used herein, "adenocarcinoma" refers to a cancerous tumor as opposed to an "adenoma" which refers to a benign (non-cancerous) tumor made up of cells that form glands (collections of cells surrounding an empty space).

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the mammal.

The term "alterations in peptide structure" as used herein refers to changes including, but not limited to, changes in sequence, and post-translational modification.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

Amino acids have the following general structure:

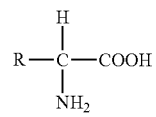

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

As used herein, the term "attach", or "attachment", or "attached", or "attaching", used herein interchangeably with "bind", or "binding" or "binds' or "bound" refers to any physical relationship between molecules that results in forming a stable complex, such as a physical relationship between a ligand, such as a peptide or small molecule, with a "binding partner" or "receptor molecule." The relationship may be mediated by physicochemical interactions including, but not limited to, a selective noncovalent association, ionic attraction, hydrogen bonding, covalent bonding, Van der Waals forces or hydrophobic attraction.

As used herein, the term "avidity" refers to a total binding strength of a ligand with a receptor molecule, such that the strength of an interaction comprises multiple independent binding interactions between partners, which can be derived from multiple low affinity interactions or a small number of high affinity interactions.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, skin, hair, tissue, blood, plasma, cells, sweat and urine.

As used herein, the term "biopsy tissue" refers to a sample of tissue that is removed from a subject for the purpose of determining if the sample contains cancerous tissue. In some embodiment, biopsy tissue is obtained because a subject is suspected of having cancer. The biopsy tissue is then examined for the presence or absence of cancer.

The term "cancer", as used herein, is defined as proliferation of cells whose unique trait—loss of normal controls—results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer.

As used herein, the term "carrier molecule" refers to any molecule that is chemically conjugated to a molecule of interest.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the cancer markers disclosed herein.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like.

Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res.

25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, the term "invasive," or "metastasis" as used herein, refers to any migration of cells, especially to invasive cancer cells or tumor cells. The term applies to normally invasive cells such as wound-healing fibroblasts and also to cells that migrate abnormally. Although the term is not to be limited by any mechanistic rationale, such cells are thought to migrate by defeating the body's means for keeping them sufficiently "in place" to function normally. Such cells are "invasive" if they migrate abnormally within a tissue or tumor, or escape the tissue, or invade other tissues.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor or target molecule.

A "receptor" or target molecule is a compound that specifically binds to a ligand.

A ligand or a receptor "specifically binds to" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

As used herein, the term "malignant" refers to having the properties of anaplasia, penetrance, such as into nearby areas or the vasculature, and metastasis.

The term "mass tag", as used herein, means a chemical modification of a molecule, or more typically two such modifications of molecules such as peptides, that can be distinguished from another modification based on molecular mass, despite chemical identity.

The term "method of identifying peptides in a sample", as used herein, refers to identifying small and large peptides, including proteins.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

As used herein, the term "peptide ligand" (or the word "ligand" in reference to a peptide) refers to a peptide or fragment of a protein that specifically binds to a molecule, such as a protein, carbohydrate, and the like. A receptor or binding partner of the peptide ligand can be essentially any type of molecule such as polypeptide, nucleic acid, carbohydrate, lipid, or any organic derived compound. Specific examples of ligands are peptide ligands of the present inventions.

The term "multimeric peptide ligand complex" refers to a complex for binding to and detecting VCAM-1 or a fragment or homolog thereof, comprising at least two peptide ligands which bind to VCAM-1. Optionally the peptide ligands are modified with conservative amino acid substitutions or additional standard or non-standards are added to enhance distribution or time before degradation, optionally additional amino acids are added as linkers, optionally moieties such as polyethylene are added to the peptide, and each of these are then attached to a chelating agent, optionally via linkers such as flexible amino acid chains, forming a multimeric peptide ligand complex. The chelating agent is useful for attachment of imaging agents. The term "multimeric peptide ligand complex" can refer to a complex with or without an imaging agent, as can the term "multimeric peptide ligand imaging complex" and the terms are meant to be used and interpreted in context. The terms can be qualified by adding the phrase with an imaging agent or the phrase without an imaging agent, or similar phrases.

The term "peptide mass labeling", as used herein, means the strategy of labeling peptides with two mass tag reagents that are chemically identical but differ by a distinguishing mass.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

As used herein, the term "post surgical tumor tissue" refers to cancerous tissue (e.g., biopsy tissue) that has been removed from a subject (e.g., during surgery).

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties. As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds, or it means that one molecule, such as a binding moiety, e.g., an oligonucleotide or antibody, binds preferentially to another molecule, such as a target molecule, e.g., a nucleic acid or a protein, in the presence of other molecules in a sample.

The terms "specific binding" or "specifically binding" when used in reference to the interaction of a peptide (ligand) and a receptor (molecule) also refers to an interaction that is dependent upon the presence of a particular structure (i.e., an amino sequence of a ligand or a ligand binding domain within a protein); in other words the peptide comprises a structure allowing recognition and binding to a specific protein structure within a binding partner rather than to molecules in general. For example, if a ligand is specific for binding pocket "A," in a reaction containing labeled peptide ligand "A" (such as an isolated phage displayed peptide or isolated synthetic peptide) and unlabeled "A" in the presence of a protein comprising a binding pocket A the unlabeled peptide ligand will reduce the amount of labeled peptide ligand bound to the binding partner, in other words a competitive binding assay.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. As used herein, the term "non-cancerous" in reference to an ovarian cell refers to a cell demonstrating regulatable cell growth and functional physiology relative to its developmental stage and activity.

As used herein, a "subject in need thereof" is a patient, animal, mammal, or human, who will benefit from the method of this invention.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

As used herein, the term "tumor" refers to an abnormal mass of tissue that results from excessive cell division that is uncontrolled and progressive. It is also called a neoplasm. Tumors may be either benign (not cancerous) or malignant.

As used herein, the term "tumor cell", as used herein, refers to any mass of cells that exhibits any uncontrolled growth patterns or altered physiology. Tumor cells may be derived from any tissue within an organism (e.g., an ovarian cell). As used herein, the term "cancer" is a general term for more than 100 diseases that are characterized by an uncontrolled, abnormal growth of cells. Cancer cells can spread locally or can intravasate and spread via the bloodstream and lymphatic system to other parts of the body and form metastases. Cancer cells that spread are called "malignant." As used herein, the terms "cancer" and "cancerous" in reference to a physiological condition in mammals is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

Other methods known in the art can be used to practice the invention. For example, imaging methods useful for the present invention can be found in Int. Pat. Pub. Nos. WO 2011/057078 (published May 12, 2011) and WO 2009/129220 (Kelly; published Oct. 22, 2009).

Embodiments

It is disclosed herein that VCAM-1 expression on mesothelial cells is correlated with ovarian tumor stage—that is, stage I ovarian cancer does not express VCAM-1 but it is expressed in stage II and stage III/4. It is also disclosed that treatment with neoadjuvant chemotherapy causes a reduction in mesothelial VCAM-1 expression and levels. VCAM-1 can be detected in vivo or in samples obtained from a subject.

The invention provides compositions and methods for detecting ovarian cancer, differentiating platinum-sensitive from platinum-resistant ovarian cancer, diagnosing platinum-sensitive or platinum-resistant ovarian cancer, monitoring the progression of cancer, or monitoring treatment of a cancer, wherein VCAM-1 expression and location is related to the cancer. The method comprises administering to a test subject a pharmaceutical composition comprising a multimeric peptide ligand complex wherein the complex comprises an imaging agent, and then detecting the imaging agent and determining the levels and location of the imaging agent in a test subject. A comparison of the levels and location in the test subject is made with the levels and location of the imaging agent from an otherwise identical location from an unaffected subject or with an unaffected area of the test subject. A higher level or different location of the imaging agent in the test subject compared with the level or location of the imaging agent in the sample from an unaffected subject or from an unaffected area of the test subject, is an indication that the test subject has a cancer or metastatic cancer associated with VCAM-1 expression in the subject. The levels or location of the detected imaging agent is an indicator of the location and amount of the biomarker VCAM-1.

In one embodiment, the present invention provides a VCAM-1 targeted peptide complex useful for imaging VCAM-1. In one aspect, the present invention provides a multimeric peptide ligand complex useful for binding to VCAM-1 or fragments or homologs thereof. In one aspect, each of the peptides that bind to VCAM-1 or a homolog or fragment thereof, independently and optionally comprise at least one non-standard amino acid substitution or conservative amino acid substitution or addition. In one aspect, each of the peptides of the multimer, independently, is optionally modified by adding at least one additional amino acid. In one aspect, each of the peptides of the multimer is independently and optionally coupled to polyethylene glycol. In one aspect, each of the peptides of the multimer or peptides optionally coupled to polyethylene glycol is further coupled to a chelating agent. Optionally the chelating agent is coupled by at least one linker to the peptides or peptides optionally coupled to polyethylene glycol. Optionally, at least one imaging agent is coupled to the chelating agent and optionally at least one therapeutic agent is coupled to the chelating agent.

In one aspect, the multimer is selected from the group consisting of a dimer, a trimer, a tetramer, pentamer, hexamer, heptamer, and octamer.

In one aspect, the method provides for the use of an imaging agent selected from the group consisting of a radionuclide, a radiological contrast agent, a paramagnetic ion, a metal, a biological tag, a fluorescent label, a chemiluminescent label, an ultrasound contrast agent and a photoactive agent. One of ordinary skill in the art will understand that the method of detection used will depend on the particular imaging agent used.

The invention further provides a method for detecting cancer, diagnosing cancer, monitoring the progression of cancer, or monitoring treatment of a cancer, wherein cells express or present VCAM-1 or a homolog or fragment thereof. The method comprises administering to a test subject a pharmaceutical composition comprising a multimeric peptide ligand complex wherein the complex comprises an imaging agent, and then detecting the imaging agent and determining the levels and location of the imaging agent in a test subject. A comparison of the levels and location in the test subject is made with the levels and location of the imaging agent from an otherwise identical location from an unaffected subject or with an unaffected area of the test subject. A higher level or different location of the imaging agent in the test subject compared with the level or location of the imaging agent in the sample from an unaffected subject or from an unaffected area of the test subject, is an indication that the test subject has a cancer associated with VCAM-1 expression or a homolog or fragment thereof. The levels or location of the detected imaging agent is an indicator of the location and amount of the biomarker VCAM-1. This method is useful for monitoring the progression of cancer and for monitoring the treatment of cancer.

In one embodiment, the cancer is a metastatic cancer. In one aspect, the cancer is ovarian cancer.

The present invention is based in part on the finding that a round of platinum-based therapy is useful for distinguishing platinum-resistant from platinum-sensitive ovarian cancer. Platinum-based chemotherapeutic agents useful for the practice of the invention include, but are not limited to, cisplatin, carboplatin, oxaliplatin, satraplatin, picoplatin, nedaplatin, triplatin, and lipoplatin. In one aspect, carboplatin is used in the methods of the invention.

Carboplatin, or cis-Diamine(1,1-cyclobutanedicarboxylato)platinum(II) (trade names Paraplatin and Paraplatin-AQ) is a chemotherapeutic agent comprising platinum that is used against some forms of cancer, such as ovarian carcinoma, lung, head and neck cancers, endometrial, esophageal, bladder, breast, cervical, central nervous system or germ cell tumors, osteogenic sarcoma, and as a preparation for a stem cell or bone marrow transplants. It can be used alone or in combination with other medications to as part of a chemotherapy cocktail or treatment regimen. Carboplatin has a M.W. of 371.25, the formula, $C_6H_{12}N_2O_4Pt$, is soluble to 25 mM in water, can be purchased with at least 99% purity, and can be stored at room temperature. In one embodiment, carboplatin is administered intravenously for a time period of at least about 5 minutes. One of ordinary skill in the art will appreciate that the dosage of carboplatin or other platinum-based chemotherapeutic agent is based on health, weight, body size, and response to therapy and that these can be used in conjunction with a known dose calculator. For example, some recent guidelines suggest that the maximum dose is based on a glomerular filtration rate (GFR) estimate that is capped at 125 mL/min for patients with normal renal function and that no higher estimated GFR values should be used.

In general, courses of carboplatin treatment should not be given more often than once every four weeks, but can be varied. It can be administered, for example, about once a week, once every two weeks, once every three weeks, once every four weeks, once every five weeks, once every six weeks, once every eight weeks and once every ten weeks. The aforementioned timing regimen is not meant to be exhaustive or exclusive and can include administering the agent at least twice per each time frame, etc.

In certain embodiments, the imaging agent is attached to the complex by a chelator. In one aspect, the chelator is DOTA.

DOTA (1,4,7,10-tetraazacyclododecane-1,4,7,10-tetraacetic acid) has the structure:

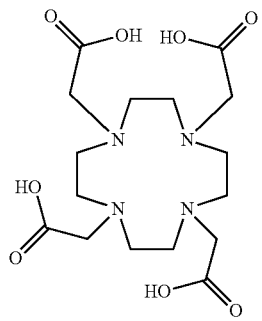

The present invention provides multimeric peptide ligand complexes useful for diagnosing, detecting, monitoring, and imaging cancer or any cell expressing VCAM-1. The peptides are used in complexes useful of imaging, diagnostics, tumor localization, etc. Methods for preparing multimeric peptides and for comparing their activity relative to the corresponding monomeric peptides, including pegylation, are described herein or can be found in the art (Li, 2007, J. Nuc. Med., 48:7:1162-1171, "[64]Cu-labeled tetrameric and octameric RGD peptides for small-animal PET of tumor $\alpha_v\beta_3$ integrin expression"; reviewed in Choe and Lee, 2007, Current Pharmaceutical Design, 13:17-31; Chen et al., 2004, Mol. Imaging Biol. 6:350-9, "MicroPET imaging of breast cancer alpha$_v$-integrin expression with $^{64}$Cu-labeled dimeric RGD peptides"; Janssen, 2002, Cancer Biother. Radiopharm., 17:641-6, "Comparison of monomeric and dimeric radiolabeled RGD-peptide for tumor targeting; Poethko, 2004, J. Nucl. Med. 45:892-902; Chen, 2004, Bioconjugate Chem., 15:41-9; Chen, 2004, Nucl. Med. Biol., 31:11-19, "Pharmacokinetics and tumor retention of $^{125}$I-labeled RGD peptide are improved by PEGylation"; Li et al., 2009, Mol. Cancer Ther., 8:5:1239-1249; U.S. Pat. No. 7,666,979 (issued from U.S. patent application Ser. No. 10/661,032); U.S. patent application Ser. No. 12/012,011 (continuation of U.S. patent application Ser. No. 10/792,582); Nahrendorf, 2010, JACC: Cardiovascular Imaging, 2:10:1213-1222; Krajewski et al., 2005, "Effect of Dimerization and Tetramerization on the Potency of HIV-Integrase Inhibitory Peptides," in Understanding Biology Using Peptides, American Peptide Society, S. Blondelle, Editor, 411-412).

The invention further includes isolated nucleic acids comprising sequences encoding peptides of the invention.

In one embodiment, the useful peptides of the invention are used to prepare multimeric peptide ligand complexes and are modified by adding additional amino acids or substituting amino acids during the synthetic process.

The present invention therefore encompasses the preparation of complexes comprising multimers of a peptide ligand, and at least one imaging agent such as a metal, radionuclide, etc., which are typically conjugated to a chelator in order to complex the imaging agent.

Chelating Agents

In some embodiments, a chelating agent may be attached to peptide, directly or indirectly, and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. patent application Ser. No. 12/112,289, incorporated herein by reference in its entirety).

Useful chelators encompassed by the invention include, but are not limited to, DTPA, DO3A, DOTA, EDTA, TETA, EHPG, HBED, NOTA, DOTMA, DFO, TETMA, PDTA, TTHA, LICAM, HYNIC, and MECAM. HYNIC is particularly useful for chelating Tc99, another imaging agent of the invention.

Modifications

The present invention further provides for the use of molecules such as polyethylene glycol ("PEG") molecules as part of the complex. In one aspect, the PEG is about 20,000 m.w. or about less than about 20,000 m.w. In another aspect, the PEG is less than about 18,000 m.w. In yet another aspect, the PEG is less that about 16,000 m.w. In a further aspect, the PEG is less than about 14,000 m.w. In a further aspect, the PEG is less than about 12,000 m.w. In a further aspect, the PEG is less than about 10,000 m.w. In a further aspect, the PEG is less than about 8,000 m.w. In a further aspect, the PEG is less than about 7,000 m.w. In a further aspect, the PEG is less than about 6,000 m.w. In a further aspect, the PEG is less than about 5,000 m.w. In a further aspect, the PEG is less than about 4,000 m.w. In a further aspect, the PEG is less than about 3,000 m.w. In a further aspect, the PEG is less than about 2,000 m.w. In a further aspect, the PEG is less than about 1,000 m.w. In a further aspect, the PEG is less than about 500 m.w.

In one aspect, the PEG is PEG5000.

Peptide Modification and Preparation

Peptide preparation is described in the Examples. It will be appreciated, of course, that the proteins or peptides of the invention may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the invention are not limited to products of any of the specific exemplary processes listed herein.

The invention includes the use of beta-alanine (also referred to as β-alanine, β-Ala, bA, and βA, having the structure:

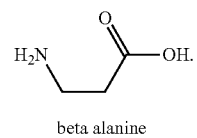

beta alanine

Sequences are provided herein which use the symbol "βA", but in the Sequence Listing submitted herewith "βA" is provided as "Xaa" and reference in the text of the Sequence Listing indicates that Xaa is beta alanine.

Peptides useful in the present invention, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxycarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high performance liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As discussed, modifications or optimizations of peptide ligands of the invention are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2', -3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Tip. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Linkers

Additionally, modifications encompassed by the invention include introduction of linkers or spacers between the targeting sequence of the binding moiety or binding polypeptide and the detectable label or therapeutic agent. For example, use of such linkers/spacers can improve the relevant properties of the binding peptides (e.g., increase serum stability, etc.). These linkers can include, but are not restricted to, substituted or unsubstituted alkyl chains, polyethylene glycol derivatives, amino acid spacers, sugars, or aliphatic or aromatic spacers common in the art.

For example, suitable linkers include homobifunctional and heterobifunctional cross-linking molecules. The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde.

Homobifunctional linker molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts.

Heterobifunctional linker molecules have at least two different reactive groups. Some examples of heterobifunctional reagents containing reactive disulfide bonds include N-succinimidyl 3-(2-pyridyl-dithio)propionate (Carlsson et al., 1978. Biochem. J., 173:723-737), sodium S-4-succinimidyloxycarbonyl-alpha-methylbenzylthiosulfate, and 4-succinimidyloxycarbonyl-alpha-methyl-(2-pyridyldithio)toluene. N-succinimidyl 3-(2-pyridyldithio)propionate is preferred. Some examples of heterobifunctional reagents comprising reactive groups having a double bond that reacts with a thiol group include succinimidyl 4-(N-maleimidomethyl)cyclohexane-1-carboxylate and succinimidyl m-maleimidobenzoate. Other heterobifunctional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-5N-hydroxy-succinimide ester.

Furthermore, linkers that are combinations of the molecules and/or moieties described above, can also be employed to confer special advantage to the properties of the peptide. Lipid molecules with linkers may be attached to allow formulation of ultrasound bubbles, liposomes or other aggregation based constructs. Such constructs could be employed as agents for targeting and delivery of a diagnostic reporter, a therapeutic agent (e.g., a chemical "warhead" for therapy), or a combination of these.

Constructs employing dimers, multimers, or polymers of one or more peptide ligands of the invention are also contemplated. Indeed, there is ample literature evidence that the binding of low potency peptides or small molecules can be substantially increased by the formation of dimers and multimers. Thus, dimeric and multimeric constructs (both homogeneous and heterogeneous) are within the scope of the instant invention. The polypeptide sequences in the dimeric constructs can be attached at their N- or C-terminus or the N-epsilon nitrogen of a suitably placed lysine moiety (or another function bearing a selectively derivatizable group such as a pendant oxyamino or other nucleophilic group), or can be joined together via one or more linkers (e.g., those discussed herein) employing the appropriate attachment chemistry. This coupling chemistry can include amide, urea, thiourea, oxime, or aminoacetylamide (from chloro- or bromoacetamide derivatives, but is not so limited). For example, methods to prepare dimeric or multimeric constructs of Pled 1 binding polypeptides of the invention include at least those discussed below.

Linkers can also be used for attachment to a chelating agent.

Therapeutic Agents

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the multimeric peptide ligand complexes described herein. Drugs useful in the invention may, for example, possess a pharmaceutical property selected from the group consisting of antimitotic, antikinase, alkylating, antimetabolite, antibiotic, alkaloid, anti-angiogenic, pro-apoptotic agents and combinations thereof.

Diagnosing, Monitoring, and Treating Ovarian Cancer

In another aspect, the invention provides compositions and methods for diagnosing a metastatic ovarian cancer in a subject. The methods include providing a sample, e.g., a biopsy sample, from a patient, and a diagnostic composition including a multimeric peptide ligand complex, wherein the peptide ligand(s) sequence is selected from, in one aspect, SEQ ID NO: 1, optionally conjugated to a detectable moiety, adding the peptide to the sample, and detecting the diagnostic composition, e.g., by detecting the detectable moiety in the sample. In some embodiments, the imaging includes but is not limited to laser scanning microscopy, immunohistochemistry, fluorescent microscopy, radiographic imaging and the like.

In a further aspect, the invention provides in vivo methods and compositions for diagnosing a metastatic ovarian cancer and whether it is platinum-resistant or platinum-sensitive. The methods include identifying a subject at risk for or suspected of having ovarian cancer; administering to a subject a diagnostic composition comprising a multimeric peptide ligand complex of the invention conjugated to an imaging molecule, and imaging the imaging molecule within the subject using in vivo imaging. In some embodiments, the ovarian cancer is a platinum-resistant cancer and in some embodiments it is a platinum-sensitive ovarian cancer. In some embodiments, the imaging molecule is a magnetofluorescent particle. In some embodiments, the magnetofluorescent particle comprises a near infrared (NIR) fluorochrome (NIRF). In some embodiments, the composition is administered via route selected from the group consisting of intradermal, subcutaneous, intraperitoneal, intravenous, intraarterial, oral, and gastric routes. In some embodiments, the in vivo imaging includes but is not limited to magnetic resonance imaging (MRI), intravital laser scanning microscopy, endoscopy, SPECT/CT, PET, and radiographic imaging.

The invention further provides for monitoring the progression of cancer, including during carcinogenesis. The present application discloses that VCAM-1 expression changes during progression and during treatment if the cancer is platinum-sensitive. The present invention provides compositions and methods for monitoring these changes.

In one embodiment, the present invention further provides compositions and methods for monitoring the progression or treatment of a cancer.

The present invention is not limited by the type of cancer associated with VCAM-1 expression.

Imaging and Diagnostic Agents

A number of trivalent metal radionuclides have physical properties suitable for radioisotope imaging (e.g., indium-111 ($^{111}$In), gallium-67/68 ($^{67/68}$Ga) and yttrium-86 ($^{86}$Y) or for targeted radionuclide therapy (e.g., $^{90}$Y and lutetium-177 ($^{177}$Lu)). These metal radionuclides can be combined with a targeting biomolecule (such as a peptide or antibody) in order to diagnose, monitor or treat disease. To obtain a radiolabeled biomolecule with the required stability, the peptide or protein must first be conjugated to a suitable chelator in order to complex the metal. The requirements of chelators for trivalent metals (such as In, Y, Ga and Lu) for labeling peptides are generally the same as those for labeling proteins. The complexes should be stable in biological systems and their chelating ability should not be impaired by reaction with the peptide. Most often, diethylenetriaminepentaacetic acid (DTPA) and/or 1,4,7,10-tetraazacyclododecane-1,4,7,10-tetraacetic acid (DOTA; CAS 60239-18-1) are used (see Choe and Lee, 2007, Current Pharmaceutical Design, 13:17-31; Li et al., 2007, J. Nuclear Medicine, "$^{64}$Cu-Labeled Tetrameric and Octameric RGD Peptides for Small-Animal PET of Tumor avb3 Integrin Expression", 48:1162-1171; Nahrendorf et al, 2009, JACC Cardiovasc. Imaging, 2:10:1213-1222; Li et al., 2009, Mol. Cancer Ther., 8:5:1239-1249; Yim et al., 2010, J. Med. Chem., 53:3944-3953; Dijkgraaf et al., 2010, Eur. J. Nucl. Med. Mol. Imaging, published online 21 Sep. 2010; U.S. patent application Ser. No. 10/792,582; Dransfield et al., U.S. Pat. Pub. Nos. US 2010/0261875; U.S. Pat. No. 7,666,979). Of the metals mentioned, the DOTA complexes are more thermodynamically and kinetically stable than the DTPA complexes (see Sosabowski et al., Nature Protocols 1,-972-976 (2006) and Leon-Rodriguez et al., Bioconjugate chemistry, Jan. 3, 2008; 19(2):391-402).

Diagnostic agents are selected from, for example, the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82}$mRb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerythrin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Techniques for detecting and measuring these agents are provided in the art or described herein.

Antibodies and their Preparation

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3, 4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

Aptamers

The present invention is also directed to useful aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

The present invention also encompasses pharmaceutical and therapeutic compositions comprising the multimeric peptide ligand complexes of the present invention. More particularly, such compounds can be formulated as pharmaceutical compositions using standard pharmaceutically acceptable carriers, fillers, solublizing agents and stabilizers known to those skilled in the art.

The present invention further provides a pharmaceutical preparation comprising one or more of the multimeric peptide ligands or complexes of the invention. The concentration of the polypeptide in the pharmaceutical composition can vary widely, i.e., from less than about 0.1% by weight, usually being at least about 1% by weight to as much as 20% by weight or more.

The composition may comprise a pharmaceutically acceptable carrier in addition to the active ingredient. The pharmaceutical carrier can be any compatible, non-toxic substance suitable to deliver the peptides o to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

Methods of producing pharmaceutical compositions comprising polypeptides are described in U.S. Pat. Nos. 5,789, 543 and 6,207,718. The preferred form depends on the intended mode of administration and therapeutic application.

In one embodiment, the present compositions comprising multimeric peptides are administered by injection. The parenteral route for administration of the polypeptide is in accordance with known methods, e.g. injection or infusion by intravenous, intraperitoneal, intramuscular, intra-arterial, subcutaneous, or intralesional routes. The protein or polypeptide may be administered continuously by infusion or by bolus injection. A typical composition for intravenous infusion could be made up to contain 10 to 50 ml of sterile 0.9% NaCl or 5% glucose optionally supplemented with a 20% albumin solution and between 10 ug and 50 mg, preferably between 50 ug and 10 mg, of the polypeptide. A typical pharmaceutical composition for intramuscular injection would be made up to contain, for example, 1-10 ml of sterile buffered water and between 10 ug and 50 mg, preferably between 50 ug and 10 mg, of the polypeptide of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

Pharmaceutical Compositions and Administration

The invention is also directed to methods of administering the compounds of the invention to a subject. In one embodiment, the invention provides a method for differentiating and for diagnosing platinum-resistant from platinum-sensitive metastatic ovarian cancer based on VCAM-1 expression and changes in VCAM-1 expression, localizing VCAM-1 expressing cells, or treating a subject by administering useful compounds based on the diagnosis made and a treatment regimen established by the treating physician based on the diagnosis. Pharmaceutical compositions comprising the useful chemotherapeutic compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the present invention to a subject in need thereof. Compounds identified by the methods of the invention can be administered with known compounds or other medications as well.

The pharmaceutical compositions useful for practicing the invention may be administered to deliver a dose of between 1 ng/kg/day and 100 mg/kg/day.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The invention is also contemplated for use in contraception for nuisance animals such as rodents.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically, dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

The invention also includes a kit comprising the composition of the invention and an instructional material which describes adventitially administering the composition to a cell or a tissue of a subject. In another embodiment, this kit comprises a (preferably sterile) solvent suitable for dissolving or suspending the composition of the invention prior to administering the compound to the subject.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the invention may, for example, be affixed to a container which contains the multimeric peptide of the invention or be shipped together with a container which contains the peptide. Alternatively, the instructional material may be shipped separately from the container with the intention that the instructional material and the compound be used cooperatively by the recipient.

Other techniques known in the art may be used in the practice of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXAMPLES

The present application tested the hypothesis that VCAM-1 is a marker of peritoneal metastasis and tumor response to platinum-based chemotherapy. The present application incorporates by reference the entirety of Scalici et al., 2013, J. Nucl. Med., 54:1883-1889, which publication is based on U.S. Provisional Pat. Application 61/806,437, filed Mar. 29, 2013.

Materials and Methods:

Patients

Following Institutional Review Board approval, the medical records of fifty-eight epithelial ovarian cancer patients undergoing treatment at the University of Virginia between 1998 and 2010 were retrospectively reviewed. Clinicopathologic data including stage at diagnosis, grade, histology, treatment regimen, and degree of surgical cytoreduction were reviewed. Among the 58 patients identified, 2 were excluded due to incomplete medical records, and 6 excluded due to inadequate tissue or staining.

After initial review of our data we noted an unexpected differential in VCAM-1 expression based on exposure to chemotherapy. Therefore we obtained additional IRB approval to identify a separate set of patients based on treatment modality: Neoadjuvant chemotherapy (NACT) versus Primary surgical cytoreduction. Thirty-two patients with advanced stage disease were identified in this subset: 18 having undergone primary surgical cytoreduction and 14 treated with NACT, one patient was excluded due to inadequate cellular material with equivocal staining.

VCAM-1 IHC

To determine whether VCAM-1 expression varied among ovarian cancer patients, we retrospectively examined the mesothelium of patients with respect to disease stage. Archived paraffin tissue blocks corresponding to each patient were evaluated or sections containing adequate amounts of mesothelial cells for review. Immunohistochemical staining for VCAM-1 was performed by the Biorepository Tissue Research Facility at the University of Virginia using human-specific anti-VCAM-1 antibodies (Abcam) according to the manufacturer's instruction. Staining was scored by a single gynecologic pathologist at our institution; expression was scored as positive (>50%) or negative (<50%).

Correlative VCAM-1 IHC

For immunohistochemical staining of mouse tissue, staining was performed by the Pathology Core at the University of Virginia using anti-VCAM antibody specific for mouse (Santa Cruz, S.C.-1504) at 5 ug/ml concentration.

Mouse Model/Cell Lines

All mouse experiments were performed in accordance with the policies and procedures established by the University of Virginia Animal Care and Use Committee. NCR nude mice (Taconic Laboratories) were injected intraperitoneally with $10^6$ SKOV3ip1 (platinum resistant), A2780 (platinum sensitive) or A2780Cis (platinum resistant) cells as previously described.

VCAM-1 Peptide

Synthesis of a SPECT imaging agent with specificity for VCAM-1 has been previously described (Kelly et al., 2006, Mol. Imaging Biol.; Nahrendorf et al., 2006 and 2009). A tetrameric VCAM-1 targeted peptide (tVCAM-4 (βAKTLLPTPGGS(PEG5000))KKKDOTAβA-NH$_2$)) (containing SEQ ID NO:1) was synthesized (CS Bio Company, Menlo Park, Calif.) for SPECT/CT imaging by chelating radioactive indium to the DOTA (Kelly, Int. Pat. Pub. No. WO 2011/057078; published May 12, 2011). For Indium labeling, the peptide (100 μg) was dissolved in 20 μl PBS, then diluted in 300 μl ammonium acetate buffer (0.1M, pH 5.5). Indium chloride (5mCi in water; Cardinal Health, Va.) was mixed with the peptide and allowed to equilibrate with mixing at 40° C. for 10 min.

Imaging of VCAM-1 in an Ovarian Metastases Model

Mice (n=3) were injected with SKOV3ip1 tumor cells as previously described then imaged 4 hours later via SPECT/ct for VCAM-1 expression. Mice were injected intraperitoneally with 1 mCi of VCAM-In$^{111}$ binding peptide. Subsequent to imaging, the uptake of labeled peptide was quantified via biodistribution and is reported as percent-injected dose per gram of mouse tissue. The imaging procedure was repeated with imaging of mice at 2, 3, and 4 weeks post tumor initiation to measure VCAM-1 signal and distribution over time.

To assess VCAM-1 as a marker of chemosensitivity, two cohorts of mice were injected with an isogenic paired cell line with one being resistant and the other sensitive to platinum: The first cohort (n=9) was injected with A2780, platinum sensitive cell line and the second (n=9) with A2780Cis platinum resistant cell line. Mice were treated with 25 mg/kg carboplatin via intra-peritoneal injection beginning 1 week after tumor initiation and weekly thereafter. Cohorts were imaged one week after tumor initiation, just prior to treatment (week 0), then 1 and 2 weeks thereafter. After each timepoint, n=3 animals from each cohort were sacrificed and VCAM-In$^{111}$ uptake quantified via biodistribution as described above.

Statistical Analysis

The significance of mesothelial VCAM-1 expression in patients was analyzed using Chi-squared and Fisher exact tests. Animal experiments were analyzed using ANOVA followed by Bonferroni Correction for all combinations.

Results

Figure 1C:
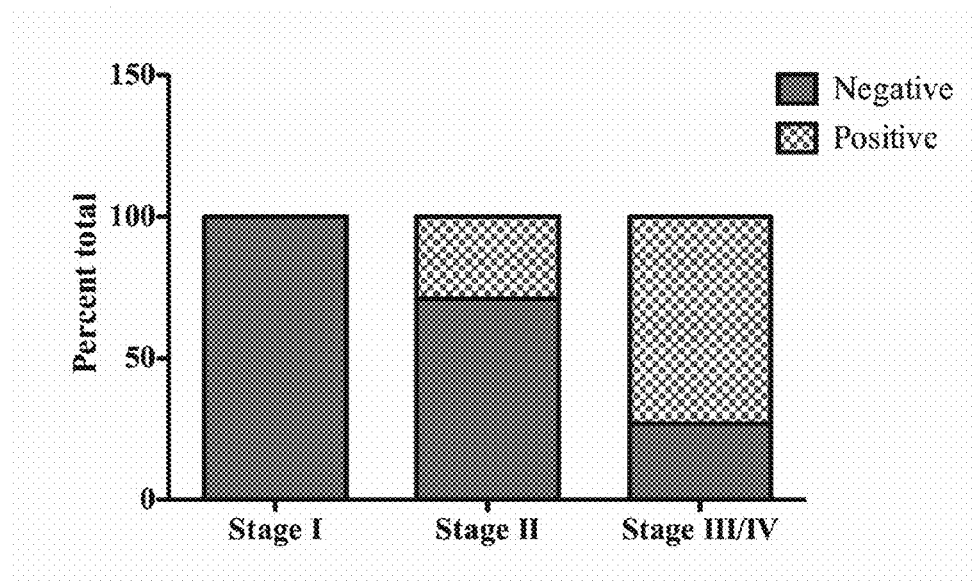
Figure 1D:
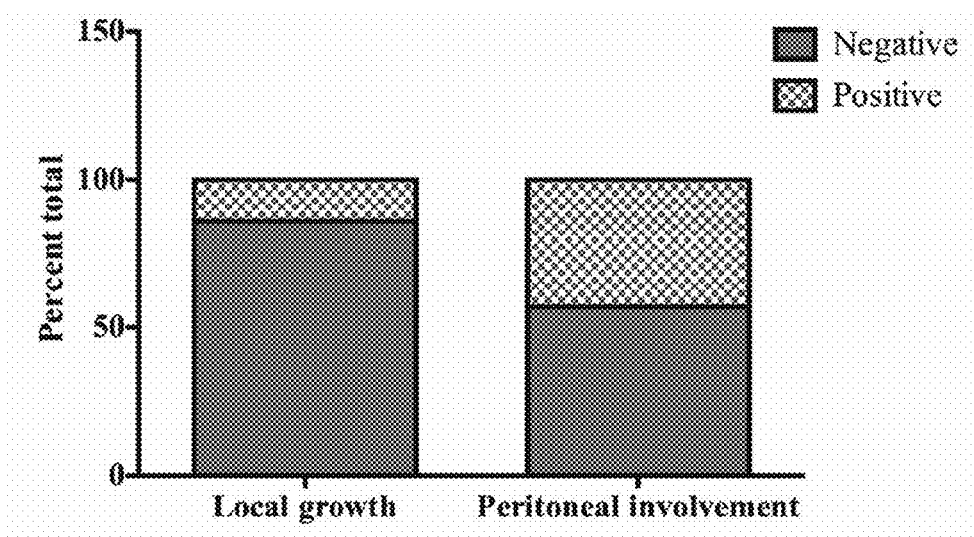

Because mesothelial VCAM-1 regulates ovarian cancer metastasis, we sought to determine when in the course of disease it is expressed and whether it would function as a marker of progression. To this end, the association between peritoneal VCAM-1 expression and clinical parameters of disease including tumor stage, optimal cytoreduction, time to recurrence and overall outcome were investigated. Fifty-six age-matched patients were identified for analysis (FIG. 1A). Biopsies of the peritoneum or omentum were examined for mesothelial VCAM-1 expression following IHC staining (FIG. 1B). The incidence of VCAM-1 expression increased with tumor stage such that none of the women diagnosed with Stage I ovarian cancer expressed VCAM-1, while VCAM-1 was detected in 4 of 14 (29%) Stage II patients and 16 of 22 (73%) of those with advanced stage (III/IV) disease, p=0.002 (FIG. 1C). To understand the discrepancies in VCAM-1 expression among Stage II or Stage III/IV patients, additional clinical and pathological features were reviewed. Stage II ovarian cancer is defined as spread within the pelvis. This definition includes the development of large tumors encompassing the primary site and adjacent tissues or the establishment of secondary tumor implants within the pelvis. Among the Stage II patients, 7 had secondary implants and 3 of those showed VCAM-1 expression; only 1 patient with primary disease showed VCAM-1 positivity (FIG. 1D). Similarly, the majority of women with Stage III/IV disease, which is characterized by extensive implantation of tumors within the entire peritoneal cavity, expressed VCAM-1 (16 of 22, FIG. 1C). These findings indicate that VCAM-1 expression is associated with peritoneal metastasis and expression is evident at the earliest indication of secondary tumor formation.

Figure 1E:
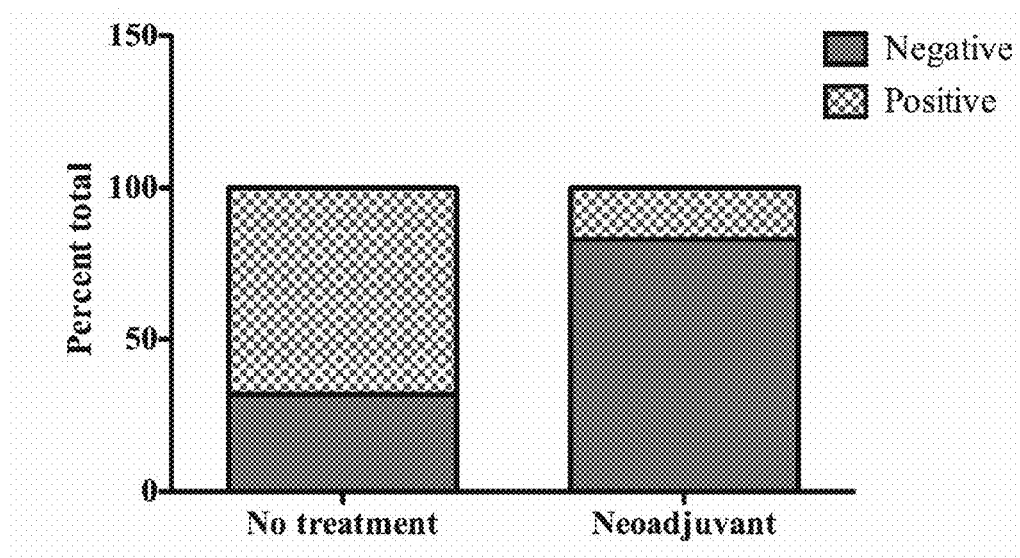

Among the patients with Stage III/IV ovarian cancer, 6 of the 22 stained specimens lacked VCAM-1 reactivity. Evaluation of the clinical data from the Stage III/IV patients indicated that 13% (4 of 30) received neoadjuvant chemotherapy (FIG. 1A), an option provided to women with excessive tumor burden in an attempt to optimize the chances of successful cytoreductive surgery. Interestingly, VCAM-1 staining was observed in just one patient who received neoadjuvant chemotherapy (data not shown). To more thoroughly evaluate the possibility that neoadjuvant chemotherapy alters VCAM-1 expression, a second set of patients including 18 undergoing primary cytoreductive surgery and 13 undergoing interval cytoreduction after neoadjuvant chemotherapy were evaluated. Analysis revealed significantly fewer women with mesothelial VCAM-1 expression following exposure to neoadjuvant chemotherapy as compared to primary surgery (15% (2 of 13) compared to 72% (13 of 18), respectively, p=0.0091) (FIG. 1E). Together, these observations indicate that in addition to the presence of VCAM-1 at the earliest stages of peritoneal spread (i.e., Stage II patients with secondary implants), expression is also responsive to treatment, thus offering the tantalizing hypothesis that VCAM-1 can be used to reflect tumor burden and predict which patients respond to platinum-based treatment.

Figure 2A:
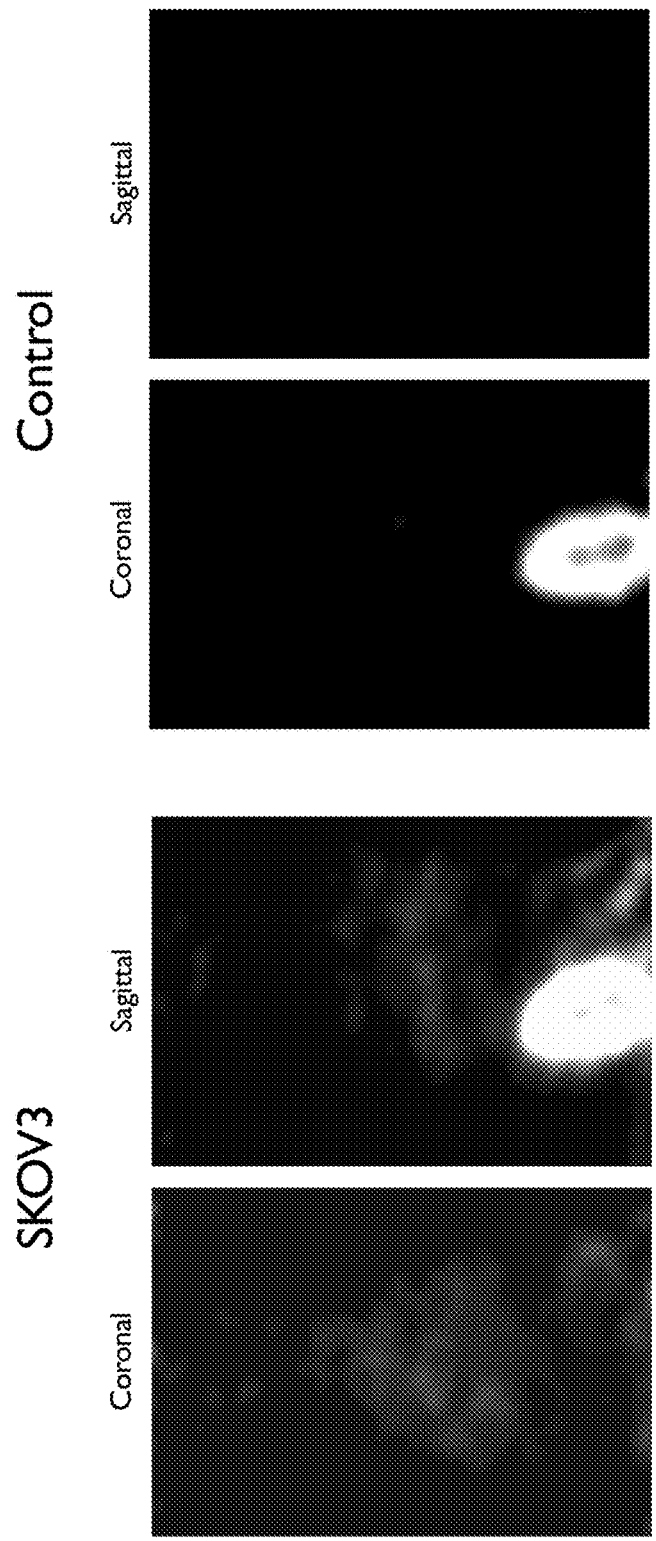
FIG. 2. Detection of mesothelial VCAM-1 expression in a mouse model of ovarian cancer peritoneal metastasis. Athymic nude mice received an intraperitoneal (IP) injection of SKOV3ip1 (SKOV3) cells or saline (control). (A) SPECT/CT imaging of VCAM-In111 peptide 4 hours after IP injection into animals. Representative coronal and sagittal sections taken from the same plane of each animal are displayed. (B) Correlative biodistribution of imaged animals. The heart and omentum were removed from each animal, and the radioactivity measured from each specimen was normalized to the gram weight of the tissue. Data are represented as percent of the dose injected per gram of tissue. (C) Correlative Histology. Following radioactive decay, the omenta were stained for VCAM-1 using IHC (60× images with 20× insert). Arrows indicate the mesothelium in each case. Top panel—mouse with SKOV3ip1 tumor cells injected; bottom panel—saline injected control mouse. (D) Kinetics of VCAM-1-In111 peptide distribution in the omentum or heart of athymic nude mice 2, 3 and 4 weeks after IP injection of SKOV3ip1 cells, n=3.
Figure 2B:
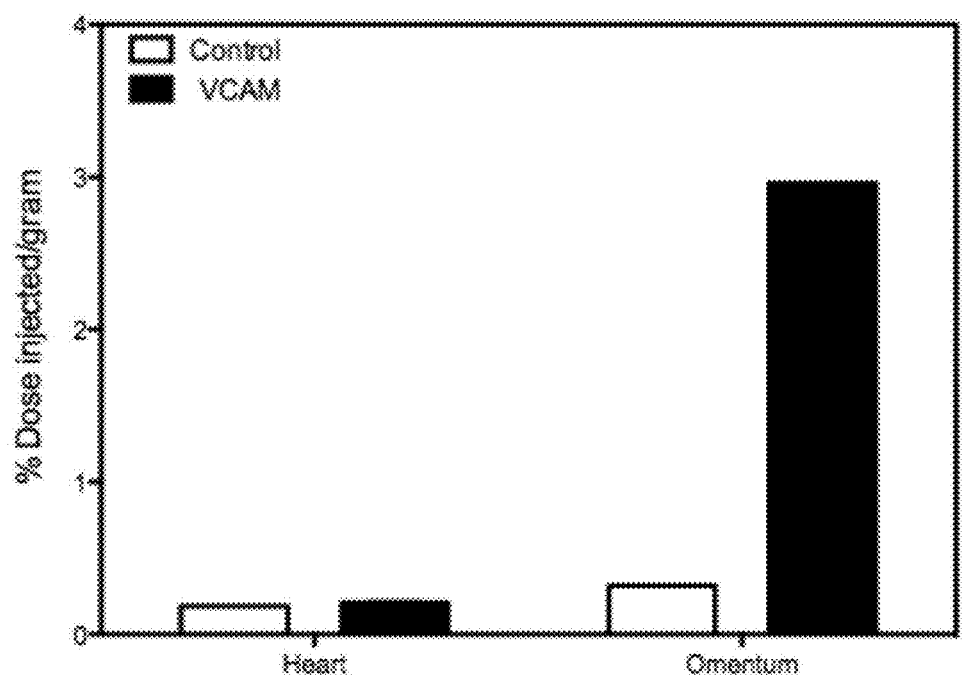
Figure 2C:
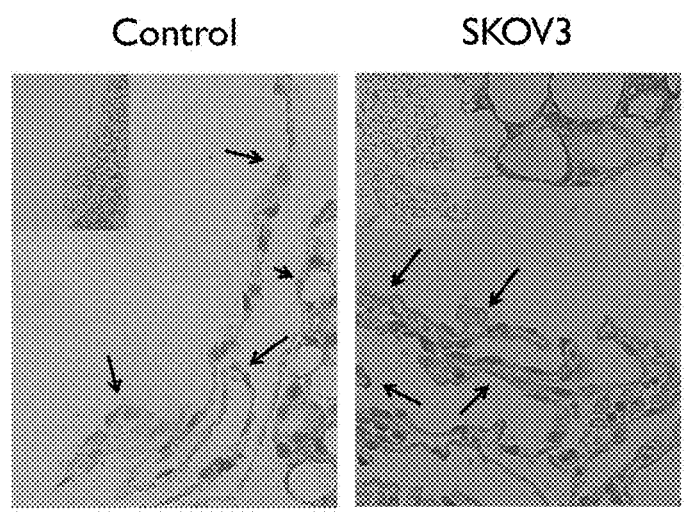
Figure 2D:
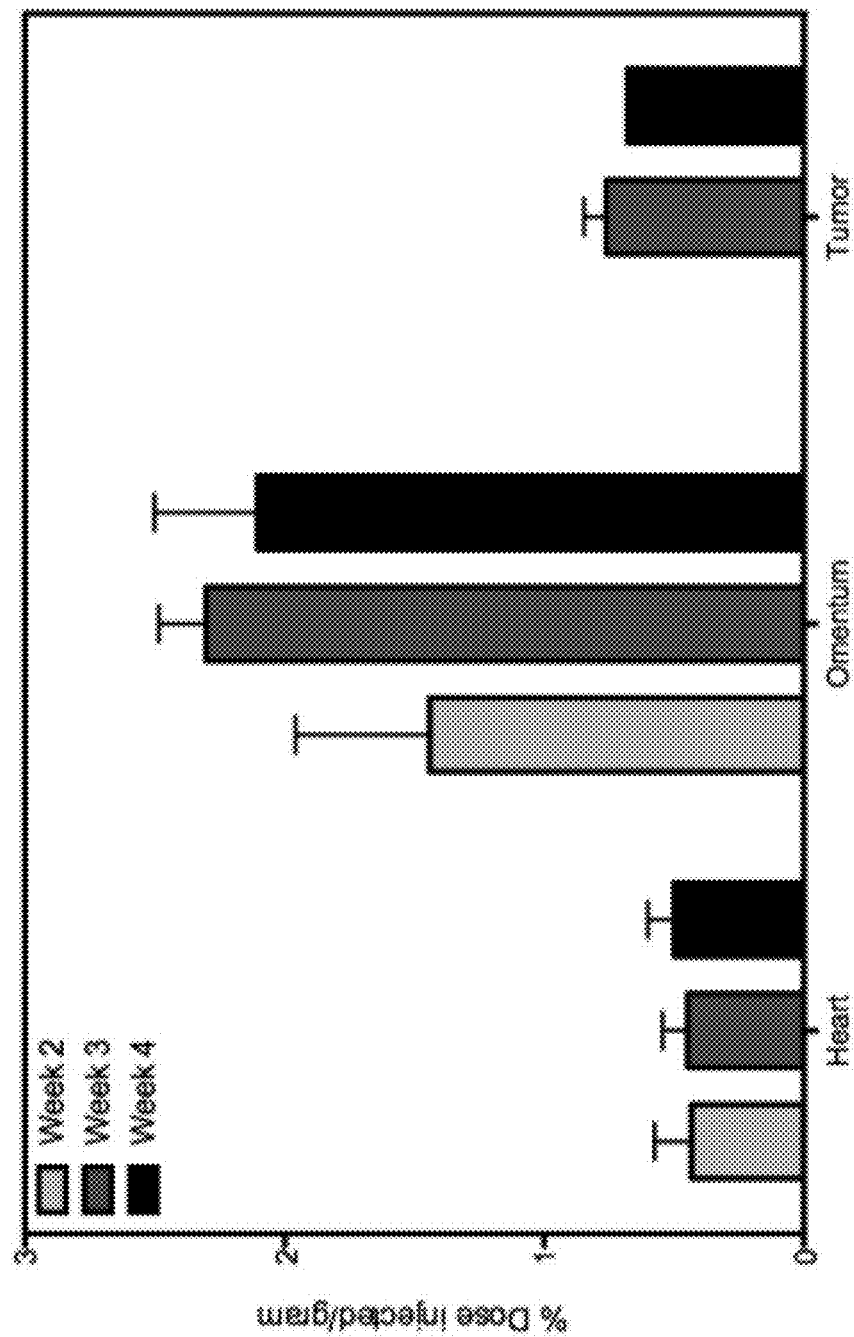

This hypothesis was tested directly in a mouse model of peritoneal ovarian cancer metastasis using SPECT/CT with VCAM-1-targeted [111]Indium-labeled imaging agent. Using IHC, we previously reported that VCAM-1 is expressed on the mesothelium of tumor-bearing mice within 2 weeks of tumor initiation, a time when tumors are microscopic. Therefore, mice were injected intraperitoneally with SKOV3ip1 cells and imaged 2 weeks later using the VCAM-1 targeted imaging agent and SPECT/CT (FIG. 2). Imaging of tumor-bearing mice demonstrated diffuse intraperitoneal labeling in regions consistent with the omentum and mesentery (FIG. 2A), primary sites of metastasis in the mouse model. In contrast, mice without tumors had kidney uptake (FIG. 2A right) consistent with kidneys being the primary route of clearance. Confirmation of imaging was provided through biodistribution analysis of omentum, mesentery and associated tumors, as well as un-involved organs such as the heart. Omentum and mesentery from tumor bearing animals had a 10 fold higher accumulation of the VCAM-1 targeted agent than omentum and mesentery from control animals (FIG. 2B). As expected, levels of VCAM-1 probe uptake in the heart were unchanged between tumor bearing animals and control animals. Correlative histology demonstrated the presence of VCAM-1 on the mesothelium of tumor bearing mice (FIG. 2C). To further refine the imaging and determine the extent and duration of expression, mice were evaluated weekly following tumor initiation starting at 2 weeks. As indicated by biodistribution, maximal VCAM-1 expression is detected 2 weeks after tumor initiation, and remains elevated through the course of the experiment (4 weeks total, FIG. 2D). Together, these observations validate the use of radiolabeled imaging probes to monitor VCAM-1 expression in a mouse model of peritoneal ovarian cancer metastasis and demonstrate that VCAM-1 is expressed early in the course of disease. However, expression does not mirror the kinetics of tumor growth; maximal VCAM-1 expression was observed with microscopic tumors and did not change as tumor burden continued to increase.

Figure 3A:
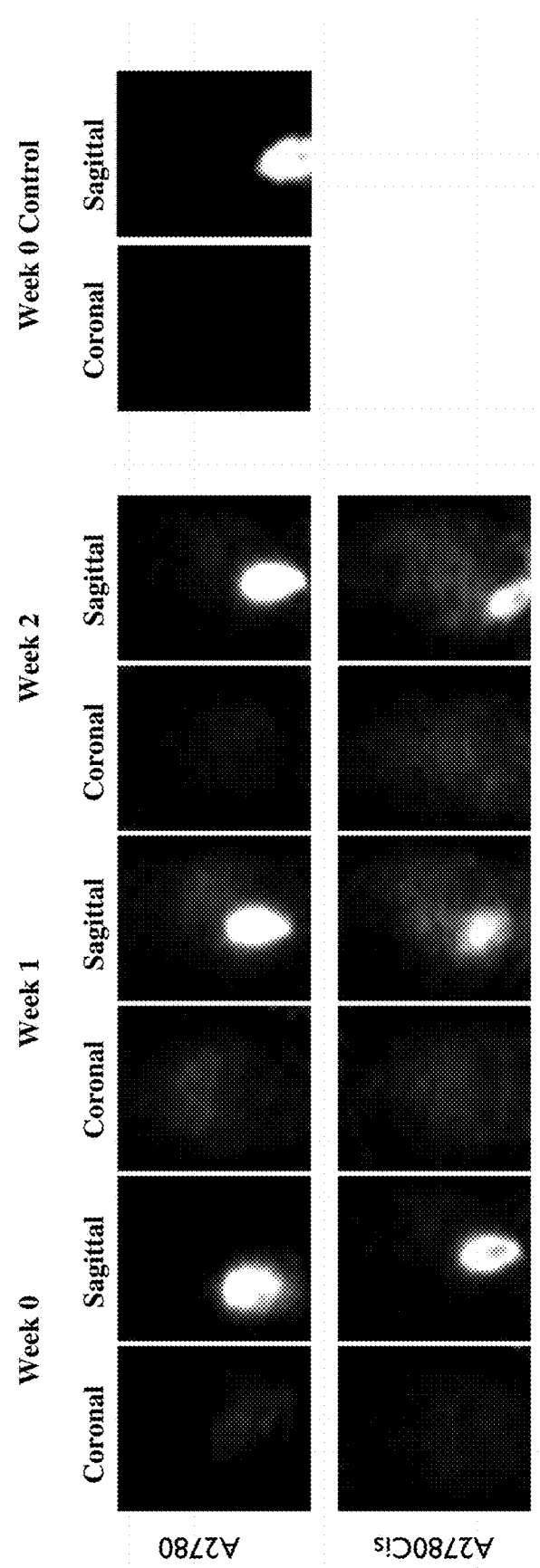
FIG. 3. Carboplatin indirectly regulates mesothelial VCAM-1 expression by affecting tumor burden. Athymic nude mice were given an intraperitoneal (IP) injection of A2780 (n=3 per time point) or A2780Cis (n=3 per time point) cells or saline (control, n=2). One week following tumor initiation a group of mice was imaged to obtain baseline values; the remaining mice were treated with 25 mg/kg carboplatin weekly. (A) SPECT/CT images were collected weekly starting 1 week after tumor initiation (week 0); weeks 0, 1 and 2 indicate that time after carboplatin treatment. Representative coronal and sagittal SPECT images (same plane for each animal) of VCAM-In111 peptide obtained 4 hours after IP injection are depicted. A2780 week 0=1.142±0.192, week 1=1.496±0.209, week 2=0.837±0.160; A2780Cis week 0=1.038±0.207, week 1=2.737±0.121, week 2=2.588±0.599. (B) Correlative biodistribution of VCAM-1 imaging probe. Heart and omentum were removed from each cohort of mice weekly post-carboplatin treatment (x-axis, 0=1 week tumor, no treatment) and the percent injected dose of radioactivity per gram of tissue determined as described above (see FIG. 2). n=3 for each cohort, C=control animals. A2780 (grey bars), a platinum-sensitive cell line, demonstrated a 1.6 fold decrease in VCAM-In111 peptide uptake when treated with carboplatin for two weeks (compare 0 to 2, grey bars, omentum). A2780Cis (platinum-resistant, black bars) demonstrated a 2.5 fold increase in uptake of VCAM-In111 peptide after two weeks of carboplatin treatment (compare 0 to 2, black bars, omentum). p<0.05, 1-way ANOVA for omentum samples; *p<0.05, Bonferroni's Multiple Comparison Test, relative to week 0, A2780. (C) Correlative histology demonstrating VCAM-1 expression on the mesothelium (arrows). At week 0, A2780 and A2780Cis show similar VCAM-1 reactivity; weeks 1 and 2 show increased VCAM-1 reactivity in mice containing A2780Cis cells compared to those with A2780 cells. Note the lack of reactivity in the control slide obtained from a mouse without tumor cells. 60× images with 20× insets. (D) Relative tumor burden among imaged mice. The omentum (primary site of tumor deposition) and any visible tumors from the peritoneal cavity were removed and weighed. Data represent mean mass±SEM (n=3); grey bars—A2780-tumored mice, black bars—A2780Cis-tumored mice. (E) Western analysis of VCAM-1 expression in mesothelial cells (LP9) treated with increasing concentrations (indicated) of carboplatin for 24 hours. Actin serves as the loading control. Representative blot of 3 experiments.
Figure 3B:
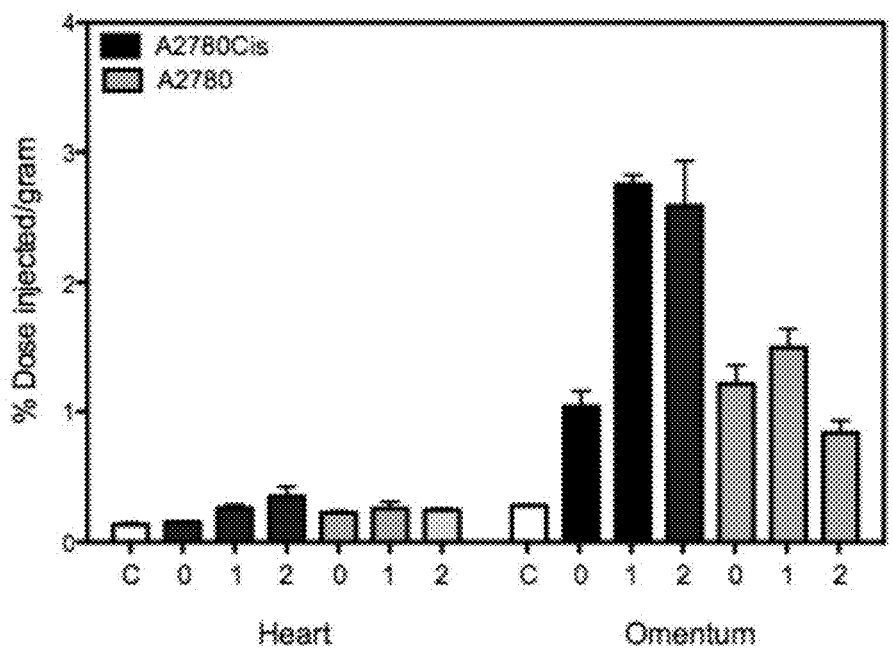
Figure 3C:
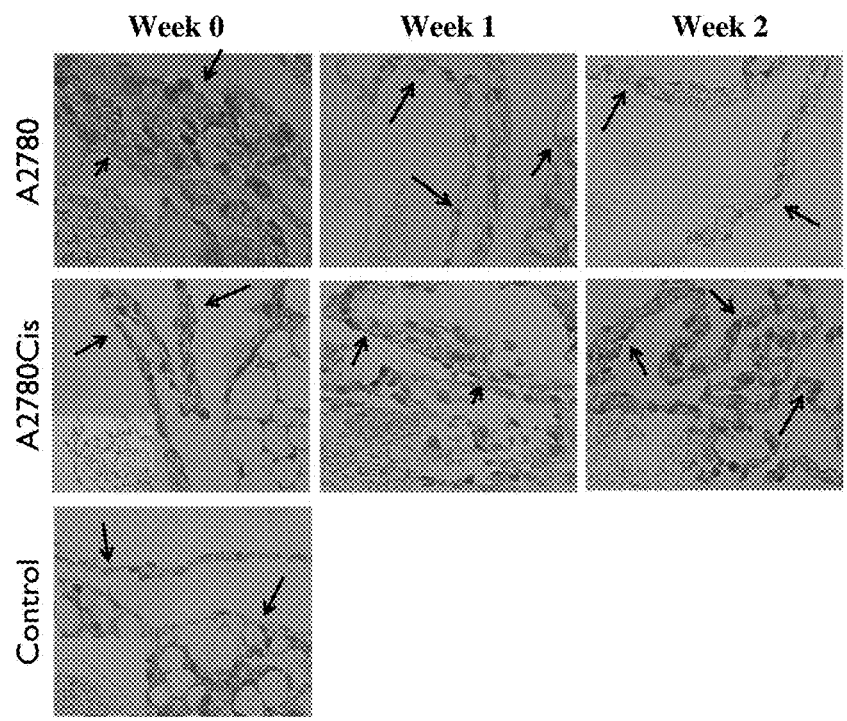
Figure 3D:
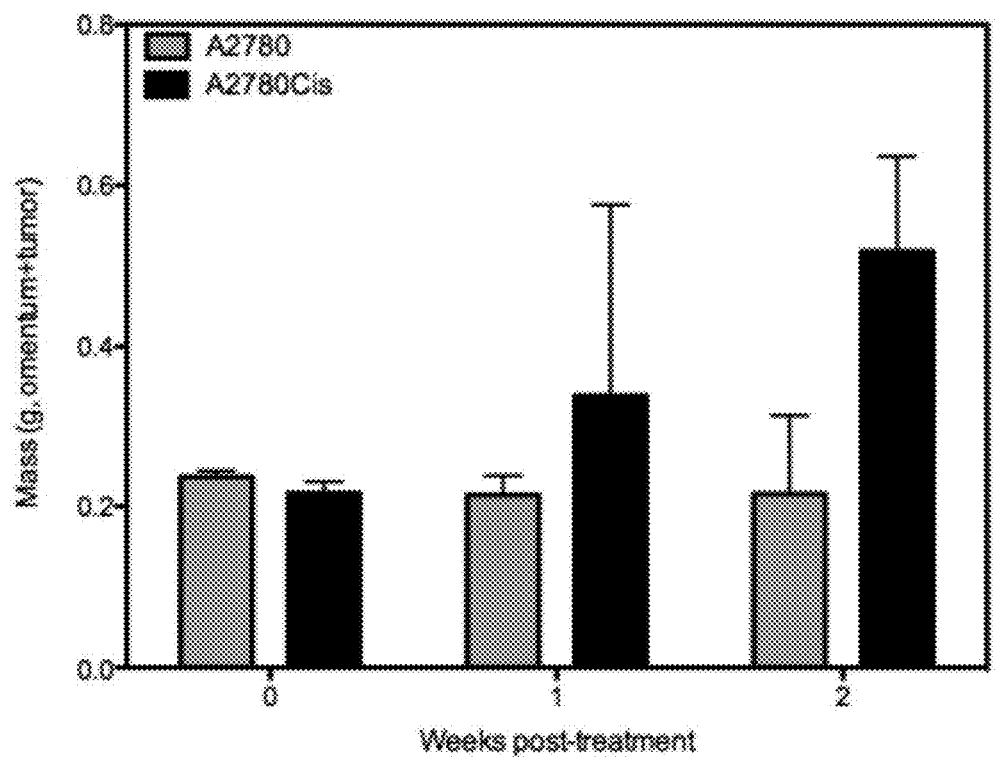
Figure 3E:
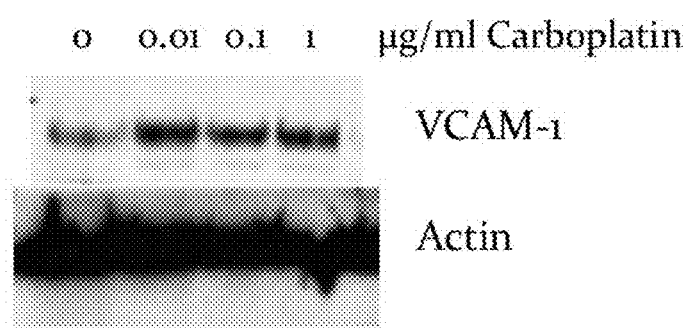
Figure 4:
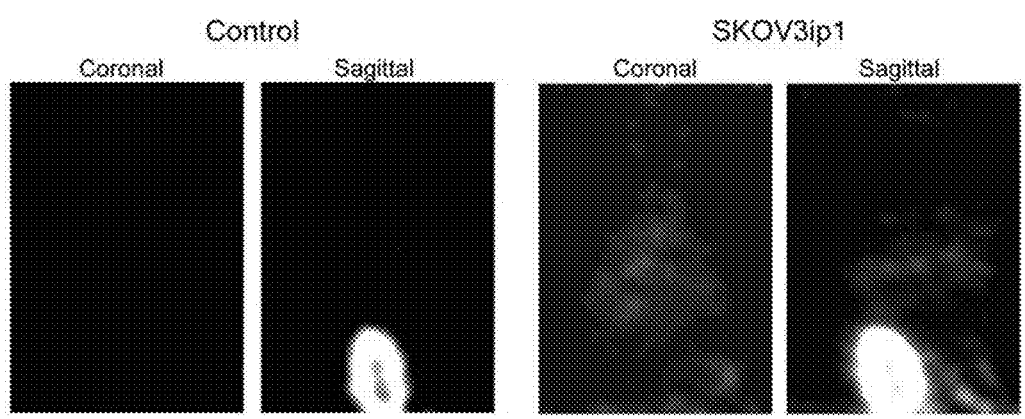
FIG. 4 (also referred to as Supplemental FIG. 1). SPECT images of 111In-tVCAM-4 peptide 4 hours after IP injection into saline control injected (Control) or tumor-bearing (SKOV3ip1) animals. Representative coronal and sagittal sections taken from the same plane of each animal are displayed.
Figure 5:
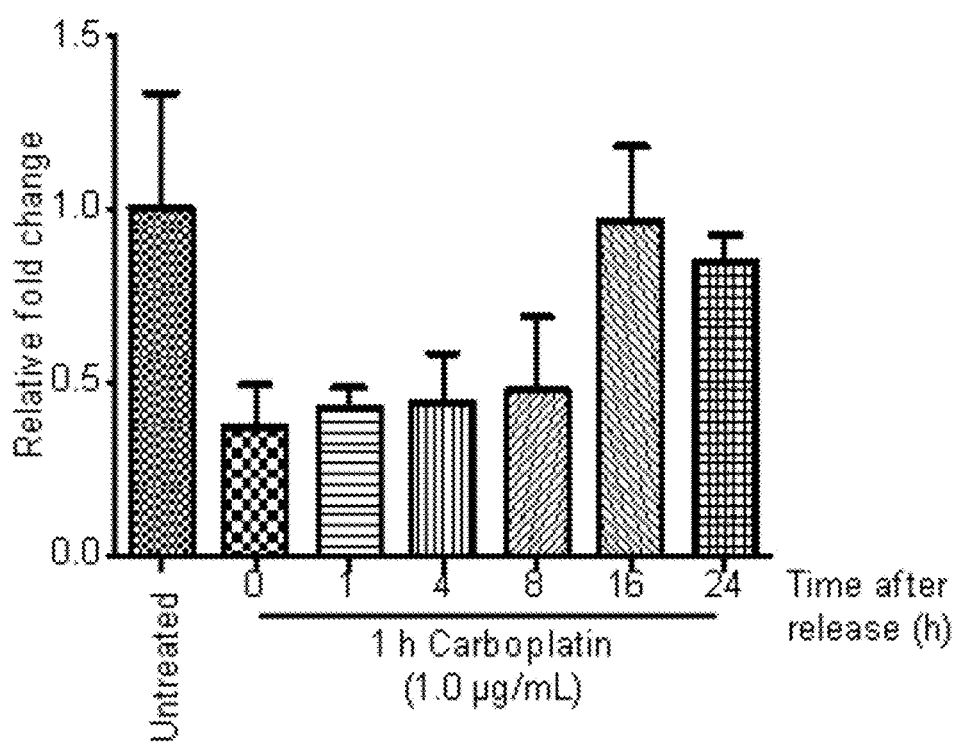
FIG. 5 (also referred to as Supplemental FIG. 2). LP9 cells treated as for FIG. 3B were subjected to qRT-PCR for VCAM-1 and GUSB (housekeeping control). Data represent the Δ-ΔCt values for each point normalized to the untreated control.
Figures 6A, 6B:
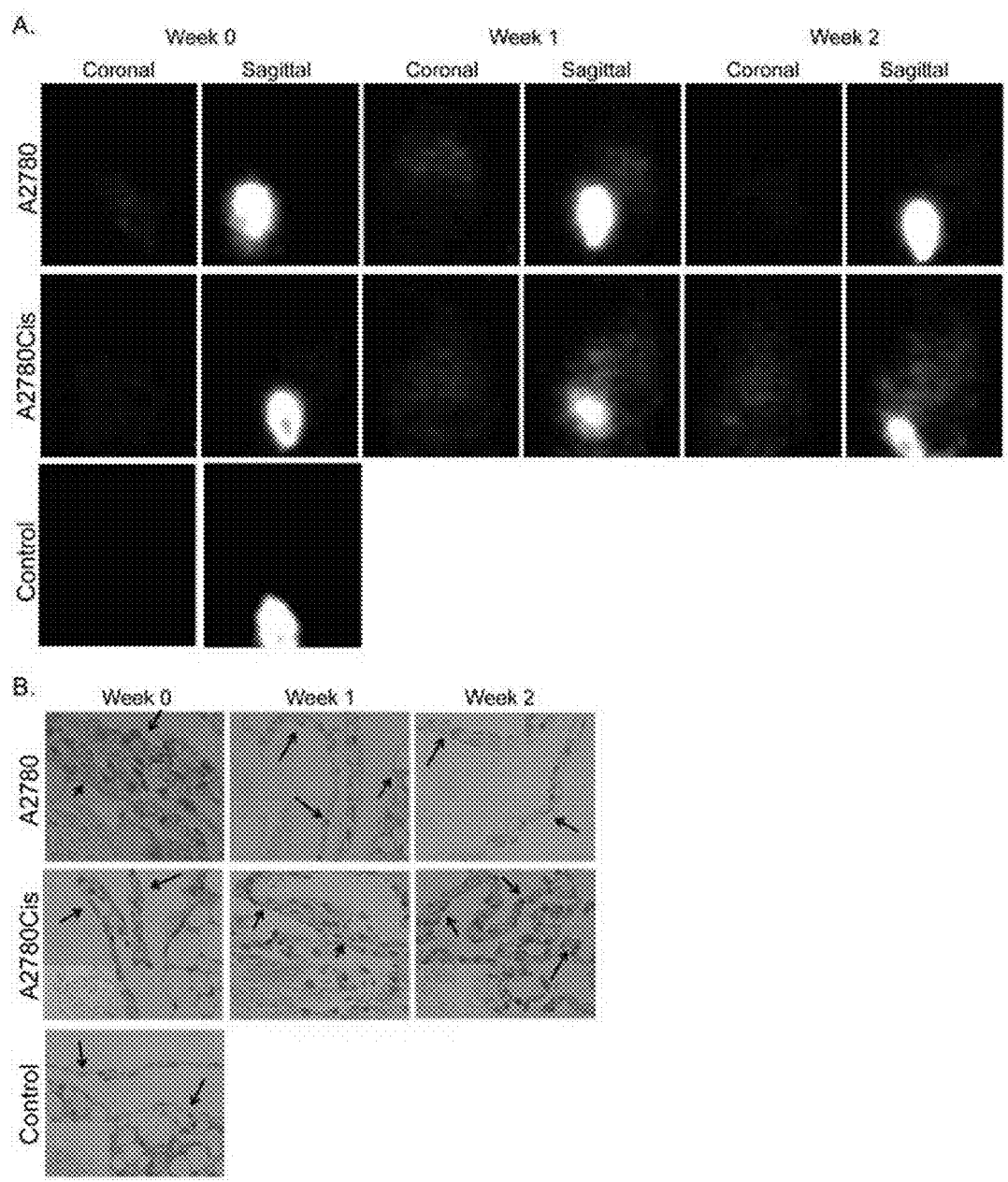
FIG. 6 (also referred to as Supplemental FIG. 3). (A) SPECT/CT images were collected weekly starting 1 week after tumor initiation (week 0) as described in FIG. 3A; weeks 0, 1 and 2 indicate time after carboplatin treatment. Representative coronal and sagittal SPECT images (same plane for each animal) of 111In-tVCAM-4 peptide obtained 4 hours after IP injection are depicted. (B) Correlative histology demonstrating VCAM-1 expression on the mesothelium (arrows). At week 0, A2780 and A2780Cis show similar VCAM-1 reactivity; weeks 1 and 2 show increased VCAM-1 reactivity in mice containing A2780Cis cells compared to those with A2780 cells. Note the lack of reactivity in the control slide obtained from a mouse without tumor cells. 60× images with 20× insets.

Our retrospective data suggests that rather than the volume of residual disease, persistent VCAM-1 expression after platinum treatment may reflect responsiveness to chemotherapy. To test this possibility, VCAM-1 expression was evaluated in mice harboring platinum-resistant (A2780Cis) or platinum-sensitive (A2780) ovarian cancer cells following treatment with carboplatin, a standard chemotherapy for the treatment of ovarian cancer. Baseline VCAM-1 expression before treatment was determined using SPECT/CT one week after tumor initiation with each cell line (FIGS. 3A and B, Week 0). Each group of mice was treated with 25 mg/kg carboplatin weekly and imaged one and two weeks following treatment. As shown in FIG. 3, VCAM-1 expression was detected 1 week after tumor initiation in both models (week 0). Tumors in mice containing A2780Cis cells continued to grow in the presence of carboplatin (FIG. 3C). Concomitantly, VCAM-1 expression in this model increased within 2 weeks of initiation and remained elevated for the duration of the experiment (3 weeks) (FIG. 3B). In contrast, omentum from animals with tumors generated from platinum sensitive A2780 cells had statistically significantly lower levels of VCAM-1 probe uptake after two weeks of treatment (FIGS. 3A,B,C). To rule out the possibility that carboplatin directly regulates mesothelial VCAM-1 expression, human mesothelial cells that constitutively express VCAM-1 were treated with increasing concentrations of carboplatin or for increasing periods of time. FIG. 3E shows no change in VCAM-1 expression in cells treated with up to 1 µg/ml carboplatin for 24 hours. These observations indicate that VCAM-1 expression mirrors tumor response to platinum-based chemotherapy and implicate VCAM-1 as a marker of therapeutic efficacy within one week of treatment.

Resistance to platinum-based treatment clearly carries a poor prognosis in ovarian cancer. Unfortunately, to date this phenomenon is defined somewhat loosely based on retrospective data; patients are categorized as having platinum resistant disease only after having failed primary therapy with persistent disease or progression within 6 months of completion of therapy. Our observations that VCAM-1 is expressed on the mesothelium of women with peritoneal ovarian cancer metastasis and is halted in platinum-sensitive cells raise the exciting possibility of using VCAM-1 as a marker of treatment response. This knowledge has potential to impact treatment decisions, i.e., to give neoadjuvant chemotherapy versus attempting a primary cytoreduction. Additionally, it may preoperatively reveal the need for radical procedures during primary debulking surgery, allow for more specific surgical planning and an increased awareness of the potential surgical morbidity. Lastly, a molecular indication of chemosensitivity could allow for earlier detection of platinum resistant disease and allow for alterations in treatment regimen directed at the molecular behavior of disease.

See also the Supplemental Figures.

Supplemental Data

SUPPLEMENTAL TABLE 1

Tissue biodistribution of $^{111}$In-tVCAM-4 in nude mice 4 hours after probe injection.

| Tissue | Mean (% dose injected/g) | Std Dev |
|---|---|---|
| Kidney | 44.24 | 12.62 |
| Liver | 0.68 | 0.06 |
| Pancreas | 0.74 | 0.23 |
| Spleen | 0.41 | 0.08 |
| Lung | 0.38 | 0.03 |
| Heart | 0.22 | 0.04 |

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Ozols, R. F. Treatment goals in ovarian cancer. International journal of gynecological cancer: official journal of the International Gynecological Cancer Society 15 Suppl 1, 3-11 (2005).
2. Eisenhauer, E. L., et al. The effect of maximal surgical cytoreduction on sensitivity to platinum-taxane chemotherapy and subsequent survival in patients with advanced ovarian cancer. Gynecologic oncology 108, 276-281 (2008).
3. Hou, J. Y., et al. Neoadjuvant chemotherapy lessens surgical morbidity in advanced ovarian cancer and leads to improved survival in stage IV disease. Gynecologic oncology 105, 211-217 (2007).
4. Rustin, G. J., et al. Early versus delayed treatment of relapsed ovarian cancer (MRC OV05/EORTC 55955): a randomised trial. Lancet 376, 1155-1163 (2010).
5. Rustin, G. J. Use of CA-125 to assess response to new agents in ovarian cancer trials. Journal of clinical oncology: official journal of the American Society of Clinical Oncology 21, 187s-193s (2003).
6. Eisenhauer, E. A. Optimal assessment of response in ovarian cancer Annals of oncology: official journal of the European Society for Medical Oncology/ESMO 22 Suppl 8, viii49-viii51 (2011).
7. Slack-Davis, J. K., Atkins, K. A., Harrer, C., Hershey, E. D. & Conaway, M. Vascular cell adhesion molecule-1 is a regulator of ovarian cancer peritoneal metastasis. Cancer Research 69, 1469-1476 (2009).
8. Kelly, K. A., et al. Detection of vascular adhesion molecule-1 expression using a novel multimodal nanoparticle. Circulation research 96, 327-336 (2005).
9. Kelly, K. A., Nahrendorf, M., Yu, A. M., Reynolds, F. & Weissleder, R. In vivo phage display selection yields atherosclerotic plaque targeted peptides for imaging. Molecular imaging and biology: MIB: the official publication of the Academy of Molecular Imaging 8, 201-207 (2006).
10. Kelly, K. A., Waterman, P. & Weissleder, R. In vivo imaging of molecularly targeted phage. Neoplasia 8, 1011-1018 (2006).
11. Nahrendorf, M., et al. Noninvasive vascular cell adhesion molecule-1 imaging identifies inflammatory activation of cells in atherosclerosis. Circulation 114, 1504-1511 (2006).
12. Cannistra, S. A., Ottensmeier, C., Tidy, J. & DeFranzo, B. Vascular cell adhesion molecule-1 expressed by peritoneal mesothelium partly mediates the binding of activated human T lymphocytes. Experimental hematology 22, 996-1002 (1994).
13. Kelly, Int. Pat. Pub. No. WO 2011/057078 (published May 12, 2011).
14. Nahrendorf, M., et al., $^{18}$F-4V for PET-CT imaging of VCAM-1 imaging of VCAM-1 expression in atherosclerosis, JACC Cardiovasc. Imaging, 2009:2:1213-1222.

What is claimed is:

1. A method for differentiating platinum-sensitive metastatic ovarian cancer from platinum-resistant metastatic ovarian cancer, said method comprising administering an effective amount of a platinum-based chemotherapeutic agent to a subject with ovarian cancer, determining the level of VCAM-1 expression in said subject following said administration and comparing said VCAM-1 level to the level of VCAM-1 expression in said subject prior to administration of said chemotherapeutic agent or to a standard value of VCAM-1 levels, wherein said VCAM-1 levels in said subject are determined by administering to said subject an effective amount of a VCAM-1 imaging probe that binds to VCAM-1 or contacting a biopsy from said subject with an effective amount of a VCAM-1 imaging probe, and then determining the amount of VCAM-1 levels in said subject or in said biopsy, wherein said VCAM-1 probe is a multimeric peptide ligand complex comprising SEQ ID NO:1, each of said peptides is coupled to polyethylene glycol, said polyethylene glycol is coupled to a chelating agent via a linking agent, and optionally at least one imaging agent is coupled to said chelating agent, wherein a decrease in VCAM-1 levels following said administration is an indication that the ovarian cancer is platinum-sensitive and no change in VCAM-1 levels is an indication that the ovarian cancer is platinum-resistant, thereby differentiating platinum-sensitive metastatic ovarian cancer from platinum-resistant metastatic ovarian cancer.

2. The method of claim 1, further wherein a cancer treatment regimen is designed and implemented based on whether the subject has a platinum-sensitive or platinum-resistant metastatic ovarian cancer, wherein when said ovarian cancer is platinum-sensitive said subject is treated with platinum-based therapy and when said ovarian cancer is platinum-resistant a non-platinum-based therapy is used to treat said subject.

3. The method of claim 1, wherein said imaging agent is a radionuclide.

4. The method of claim 3, wherein said radionuclide is $^{111}$In.

5. The method of claim 1, wherein said probe has the formula [(VHPKQHRGGSPEG5K)4K]2-KK(DOTA)-βA-NH$_2$ (tVCAM-4).

6. The method of claim 5, wherein said probe is $^{111}$In-tVCAM-4.

7. The method of claim 6, wherein said imaging agent is detected with a single photon emission computed tomography/computed tomography (SPECT/CT) scanner coupled to a computer, and imaging data are collected and analyzed using a program to quantify or compare levels of VCAM-1.

8. The method of claim 7, further wherein the location of said imaging agent is determined.

9. The method of claim 1, wherein said platinum-based chemotherapeutic agent is selected from the group consisting of cisplatin, carboplatin, oxaliplatin, satraplatin, picoplatin, nedaplatin, triplatin, and lipoplatin.

10. The method of claim 1, further comprising the step of diagnosing platinum-sensitive or platinum-resistant ovarian cancer.

11. The method of claim 1, further comprising reporting the indication of platinum-sensitive or platinum-resistant ovarian cancer to the subject or physician.

12. The method of claim 1, further wherein the VCAM-1 levels are monitored during treatment by detecting and measuring VCAM-1 levels.

13. The method of claim 1, further wherein the progression of the ovarian cancer is monitored by detecting and measuring VCAM-1 levels.

* * * * *

```
SEQUENCE LISTING

<160> NUMBER OF SEQ ID NOS: 1

<210> SEQ ID NO 1
<211> LENGTH: 10
<212> TYPE: PRT
<213> ORGANISM: homo sapiens

<400> SEQUENCE: 1

Val His Pro Lys Gln His Arg Gly Gly Ser
1               5                   10
```